(12) United States Patent
Woo et al.

(10) Patent No.: US 12,272,264 B2
(45) Date of Patent: Apr. 8, 2025

(54) MITRAL VALVE ANNULAR DILATION DEVICES AND METHODS FOR USE

(71) Applicant: THE BOARD OF TRUSTEES OF THE LELAND STANFORD JUNIOR UNIVERSITY, Stanford, CA (US)

(72) Inventors: Y. Joseph Woo, Stanford, CA (US); Michael John Paulsen, Los Altos, CA (US); Cole C. Paullin, Manhatten Beach, CA (US); Annabel M. Imbrie-Moore, Stanford, CA (US); Tabitha Marie Bandy-Vizcaino, Stanford, CA (US)

(73) Assignee: The Board of Trustees of the Leland Stanford Junior University, Stanford, CA (US)

(*) Notice: Subject to any disclaimer, the term of this patent is extended or adjusted under 35 U.S.C. 154(b) by 564 days.

(21) Appl. No.: 17/672,606

(22) Filed: Feb. 15, 2022

(65) Prior Publication Data
US 2022/0172646 A1 Jun. 2, 2022

Related U.S. Application Data

(63) Continuation of application No. PCT/US2020/047268, filed on Aug. 20, 2020.

(60) Provisional application No. 62/889,520, filed on Aug. 20, 2019.

(51) Int. Cl.
*G09B 23/32* (2006.01)
*G09B 23/30* (2006.01)

(52) U.S. Cl.
CPC .......... *G09B 23/32* (2013.01); *G09B 23/303* (2013.01)

(58) Field of Classification Search
CPC ......... G09B 23/28; G09B 23/30; G09B 23/32
See application file for complete search history.

(56) References Cited

U.S. PATENT DOCUMENTS

| 9,539,094 | B2* | 1/2017 | Dale | A61B 17/0644 |
|---|---|---|---|---|
| 2007/0254273 | A1* | 11/2007 | LaFrance | A61F 2/2472 434/272 |
| 2014/0272867 | A1* | 9/2014 | Ratcliffe | G09B 23/28 434/262 |
| 2021/0350723 | A1* | 11/2021 | Pirlot | G09B 23/30 |
| 2022/0246064 | A1* | 8/2022 | Takeuchi | G09B 23/30 |
| 2022/0287708 | A1* | 9/2022 | Cortez, Jr. | A61B 17/04 |

FOREIGN PATENT DOCUMENTS

WO WO-2017165969 A1 * 10/2017

* cited by examiner

*Primary Examiner* — Kurt Fernstrom
(74) *Attorney, Agent, or Firm* — William A. English; Vista IP Law Group LLP

(57) ABSTRACT

A dilation device is provided for modeling mitral regurgitation in a mitral valve that includes an annular housing surrounding an aperture; a first anterior blade mounted to the housing and defining a substantially straight inner edge adjacent the aperture; and a plurality of posterior blades mounted to the housing and defining a curved inner edge adjacent the aperture, the posterior blades movable to dilate a valve mounted to the blades. An annulus of a valve may be sutured to the blades such that valve is disposed adjacent the aperture, and the dilation device may be actuated to cause the posterior blades to dilate a posterior region of the valve.

20 Claims, 21 Drawing Sheets

Table 1 – Hemodynamic Parameters

|  | Baseline | Pre-Threshold Dilation | Max Dilation |
|---|---|---|---|
| Heart rate (bpm) | 70.00 ± 0.00 | 70.00 ± 0.00 | 70.00 ± 0.00 |
| Mean arterial pressure (mmHg) | 106.69 ± 0.22 | 100.35 ± 4.38 | 68.10 ± 9.66 |
| Diastolic pressure (mmHg) | 89.07 ± 1.62 | 83.71 ± 5.00 | 55.51 ± 9.57 |
| Systolic pressure (mmHg) | 125.01 ± 1.36 | 117.90 ± 3.71 | 83.09 ± 10.11 |
| Mean atrial pressure (mmHg) | 6.94 ± 1.18 | 5.93 ± 0.87 | 5.89 ± 0.10 |
| Mean ventricular pressure (mmHg) | 47.66 ± 0.95 | 45.80 ± 1.66 | 32.26 ± 3.62 |
| Cardiac output (liters/min) | 3.52 ± 0.21 | 3.92 ± 0.54 | 3.22 ± 0.71 |
| Effective stroke volume (ml) | 50.26 ± 3.04 | 56.00 ± 7.77 | 46.02 ± 10.10 |
| Pump stroke volume (ml) | 109.83 ± 0.03 | 109.81 ± 0.18 | 109.84 ± 0.15 |
| Mitral valve mean gradient (mmHg) | -2.27 ± 1.10 | -2.95 ± 0.99 | -0.86 ± 1.21 |
| Mitral valve mean back pressure (mmHg) | 105.38 ± 2.82 | 100.20 ± 2.62 | 64.98 ± 9.18 |
| Mitral forward flow time (sec) | 0.53 ± 0.00 | 0.52 ± 0.01 | 0.53 ± 0.00 |
| Mitral forward volume (ml) | 66.09 ± 2.71 | 74.29 ± 7.45 | 86.42 ± 7.95 |
| Mitral valve RMS forward flow (ml/sec) | 216.28 ± 66.40 | 301.76 ± 77.74 | 366.21 ± 50.73 |
| Mitral regurge fraction (%) | 23.91 ± 4.27 | 24.83 ± 4.31 | 47.15 ± 7.80 |
| Mitral leakage rate (ml/sec) | -32.77 ± 13.75 | -40.27 ± 9.44 | -108.73 ± 13.13 |
| Mitral leakage volume (ml) | -8.77 ± 3.47 | -11.04 ± 2.55 | -27.85 ± 2.67 |
| Mitral closing volume (ml) | -7.05 ± 1.04 | -7.27 ± 0.31 | -12.57 ± 2.50 |
| Ventricular energy (mJ) | 1012.10 ± 68.10 | 1001.63 ± 80.72 | 797.92 ± 105.88 |
| TransMitral forward energy loss (mJ) | 16.02 ± 9.00 | 1.51 ± 5.98 | 10.17 ± 17.88 |
| TransMitral closing energy loss (mJ) | 34.58 ± 5.88 | 35.70 ± 3.07 | 62.37 ± 8.95 |
| TransMitral leakage energy loss (mJ) | 124.48 ± 45.79 | 150.09 ± 33.54 | 243.97 ± 12.31 |
| TransMitral total energy loss (mJ) | 175.08 ± 55.35 | 187.31 ± 41.34 | 316.50 ± 20.02 |

Data presented as mean ± standard deviation. p-values calculated using non-parametric Friedman tests

*Fig. 7*

MITRAL VALVE ANNULAR DILATION DEVICES AND METHODS FOR USE

RELATED APPLICATION DATA

The present application is a continuation of co-pending International Application No. PCT/US2020/047268, filed Aug. 20, 2020, which claims benefit of U.S. provisional application Ser. No. 62/889,520, filed Aug. 20, 2019, the entire disclosures of which are expressly incorporated by reference herein.

FIELD OF THE INVENTION

The present invention relates to medical devices, and, more particularly, to valve dilation devices, e.g., dilation devices configured to selectively dilate the posterior annulus of an explanted mitral valve, simulating in vivo mitral valve annular dilation, and to systems and methods for using such dilation devices, e.g., to simulate mitral valve repair procedures.

BACKGROUND

Mitral regurgitation ("MR") due to annular dilation occurs secondary to a variety of mitral valve diseases and is observed in a majority of heart failure patients. To understand the biomechanics of MR and ultimately design the optimal annuloplasty ring, a representative disease model is needed. However, accurately simulating this disease state is challenging due to the asymmetric dilation of the mitral annulus.

Valvular heart disease is a common cause of morbidity and mortality globally and affects approximately 2.5% of the United States population. The most prevalent cause of valvular heart disease is mitral regurgitation. There are several causes of mitral regurgitation, including primary disease of the mitral valve apparatus (e.g., rupture of the chordae tendineae, failure of the leaflets, papillary muscle dysfunction, and infectious disease) and secondary regurgitation due to left ventricular enlargement. As the heart experiences MR, the left ventricle ("LV") dilates over time to compensate for reduced forward stroke volume. This enlargement of the LV leads to an increase in the annulus size, which further worsens MR. Thus, regardless of etiology, most patients with chronic MR exhibit some degree of mitral annular dilation and highly asymmetrically with the predominant dilation occurring across the posterior annulus.

Ring annuloplasty is an essential component of surgical repair operations for MR. By using an annuloplasty ring to restore the pathophysiologically dilated annulus to a normal diameter, leaflet coaptation is improved and further annular dilation is prevented. Many annuloplasty ring variations exist, although there is little data on which has the most optimal geometry and material composition. It has been shown that flexible rings result in better mitral valve function after implantation compared to rigid rings, and also that saddle-shaped conformations result in better coaptation and lower forces on the ring itself.

Moreover, some reports have observed that complete rings may prevent MR recurrence more effectively compared to partial rings. Nevertheless, a recent literature review states that, due to the underpowered nature of published datasets, it is impossible to determine a statistically significant difference between any of the thirty seven different annuloplasty rings that were studied.

In order to understand the biomechanics of MR and ultimately design the optimal annuloplasty ring, a representative disease model is needed. However, accurately simulating mitral annular dilation in ex vivo experimentation is challenging due to the selective posterior dilation of the annulus. Though there has been one previous ex vivo dilation model utilizing adjustable segments to dilate the annulus, the goal of the present application is to develop a device capable of mimicking the asymmetric annular dilation state ex vivo with a continuous dilation profile and the ability to conveniently test annuloplasty ring designs under varying amounts of valve dilation.

SUMMARY

The present invention is directed to medical devices, and, more particularly, to valve dilation devices, e.g., dilation devices configured to selectively dilate the posterior annulus of an explanted mitral valve, simulating in vivo mitral valve annular dilation, and to systems and methods for using such dilation devices, e.g., to model mitral valve dilation, mitral regurgitation or other disease, and/or repair of the valve.

To accurately model mitral annular dilation, the dilation device mimics the D-shape of a natural mitral valve annulus while dilating the posterior annulus. The posterior leaflet may be dilated with negligible, or a smaller, dilation of the anterior annulus. In one embodiment, the dilation device generally includes an annular housing defining an aperture and a plurality of, e.g., five, overlapping aperture blades, with a first of the blades, i.e., an anterior blade, featuring a straight inner edge. The anterior section of an explanted valve annulus may be sewn to the straight inner edge of the anterior blade such that the anterior annulus does not dilate substantially, or dilates a small amount. The posterior annulus is sewn to the other, e.g., four, blades, which are movable from a relaxed position (wherein the blades are position toward a center of the aperture) to a dilating position (wherein the blades are positioned outwardly from the relaxed position toward a perimeter of the aperture) to dilate the posterior annulus. In one embodiment, the blades of the dilation device are 3D-printed, e.g., using cyanate ester or other strong and/or rigid plastic that allows for the extremely thin (e.g., about 0.62 mm or less) blades required for the device to fit in a left heart simulator. In another aspect, the blades of the dilation device may be formed of a flexible material, such as an elastomer polymer or other suitable material, which allows the anterior blades and/or posterior blades to flex laterally (i.e., out of the plane of the blades)to simulate substantially natural motion of a mitral valve during a cardiac cycle of a mitral valve.

Optionally, small perforations may be included along the inner border of the blades to facilitate suturing to the valve annulus. The blades may also include pins on both ends, e.g., one pointed up and one down, that fit into a stationary base plate and pivot plate, respectively. The base plate may be formed from elastic polyurethane or other rubbery material to create a hemodynamic seal around the valve and also to facilitate easy suturing.

In another aspect, the pivot plate is movable relative to the base plate, and each of the posterior blades has a first end coupled to the pivot plate such that movement of the pivot plate causes the posterior blades to move between a relaxed position and a dilating position. In another aspect, the pivot plate is rotatable relative to the base plate to cause the posterior blades to move radially outwardly to dilate the anterior annulus of a mitral valve mounted to the posterior blades. In another aspect, the base plate comprises a plurality of slots, and each of the posterior blades comprises a second end coupled to a respective slot in the base plate such that the second end moves radially inward and outward when the pivot plate moves.

In another aspect, the pivot plate is rotatable relative to the base plate to cause the posterior blades to move radially outward to dilate an anterior annulus of a mitral valve mounted to the posterior blades.

In another aspect, the dilation device further comprises a ring spacer (e.g., also formed of cyanate ester) which separates the base plate of the device from an additional stationary top plate. The top plate surrounds a raised section of the pivot plate. This spacer allows for pressure to be applied to the top plate (transmitted to the spacer and to the base plate) in order to establish a seal between the heart simulator left ventricular chamber and the bottom plate, while not impeding the pivot plate's freedom to turn.

In still another aspect, the dilation device may include a biasing mechanism coupled to the posterior blades which biases the posterior blades toward the dilating position, while allowing the posterior blades to move toward the relaxed position against the biasing mechanism. This allows the dilation device to better allow the mitral valve manipulated, re-shaped and/or influenced by a surgical repair, such as during implantation of an annuloplasty ring. An annuloplasty ring restores the pathophysiologically dilated annulus to a normal diameter (i.e., the ring reduces the diameter of the annulus). The use of a biasing mechanism allows the surgical repair being tested to reduce the diameter of the annulus after it has been dilated by the dilation device so that various surgical repairs and devices can be tested under accurate annular dilation states and under various amounts of dilation provided by the dilation device.

In another aspect of the dilation device, the biasing mechanism may be a spring coupled to the pivot plate. The spring biased pivot plate allows the pivot plate to be moved to dilate a mitral valve to simulate a defectively dilated valve, while allowing the pivot plate to move to permit the anterior blades to move toward the relaxed position and slightly constricting the valve against the biasing mechanism. The dilation device may include a locking mechanism which prevents the pivot plate and/or anterior blades from moving to a more dilated position, but which allows the pivot plate and/or anterior blades to move toward the relaxed position against the force of the biasing mechanism.

In yet another aspect, the anterior blade and posterior blades are laterally flexible to allow the anterior blade and posterior blades to flex laterally, i.e., out of the plane of the device, to allow motion of a mitral valve during a cardiac cycle of a mitral valve. The lateral movement substantially simulates the natural movement of an in vivo mitral valve.

Another embodiment of the present disclosure is directed to a system for modeling mitral regurgitation in a mitral valve. The system may utilize any of the dilation devices disclosed herein. In one embodiment, the system includes a dilation device disclosed herein, and a heart simulator. The heart simulator includes a housing for mounting the dilation device at a position in the heart simulator corresponding to a mitral valve of a heart. The heart simulator has a pump for directing fluid through the housing such that fluid passed through a valve mounted in the dilation device. In other aspects and features of the system, the dilation device may include any one or more of the additional aspects described herein.

Another embodiment of the present disclosure is directed to a method of using the dilation devices and systems disclosed herein to model mitral regurgitation in a mitral valve. In one embodiment, the method includes providing a dilation device as disclosed herein. An annulus of a valve is secured to the blades of the dilation device such that the valve is disposed within the aperture of the dilation device. The dilation device is actuated to cause the posterior blades of the dilation device to dilate a posterior region of the annulus.

In another aspect of the method, the annulus may be secured to the blades by directing one or more sutures through perforations along the inner edge and the annulus.

In another aspect of the method, during actuation of the dilation device, an anterior region of the annulus of the valve (and the anterior blade) does not dilate substantially. The term "does not dilate substantially" and similar terms with respect to an element means that such element dilates less than 20%, of the dilation of an element having the most dilation during actuation of the dilation device. Alternatively, during actuation of the dilation device, the device dilates the anterior annulus (and anterior blade) a smaller amount than the dilation of the posterior annulus (and posterior blades), such as less than 30%, or less than 40%, or less than 50%, of the dilation of the posterior annulus (and posterior blades).

In still another aspect, the method further includes mounting the dilation device with the valve secured thereto within a heart simulator, and directing fluid through the simulator such that fluid passes through the valve mounted to the dilation device to simulate operation of the valve.

In yet another aspect, the method also includes the dilation device being actuated to sequentially increase the amount of posterior dilation of the valve to analyze mitral regurgitation.

Another embodiment of the present disclosure is directed to using the dilation devices disclosed herein in reverse to correct annular dilation. In other words, a valve is mounted to the dilation device by securing an annulus of the valve to the blades of the dilation device such that the valve is disposed within the aperture. The dilation device is then actuated to cause the blades to constrict the posterior region of annulus of the valve, i.e., move the posterior region inward toward the center of the aperture/valve. This movement of the posterior region acts to repair a valve suffering from annular dilation, and/or prevents further annular dilation.

Another embodiment of a dilation device to selectively dilate the posterior annulus of an explanted mitral valve utilizes adjustment pins to selectively dilate a valve. The dilation device can be used for the same uses and purposes as the dilation device having the dilating blades. The dilation device includes a base plate having a plate aperture and a recess surrounding the aperture. A mounting ring having a ring aperture is mounted in the recess of the base plate with the ring aperture aligned with the plate aperture. A plurality of adjustment pins are mounted on the base plate and spaced angularly around the mounting ring. Each of the adjustment pins is configured to receive a respective adjustment cord. The adjustment cords are attachable to a valve mounted on the mounting ring. The adjustment cords are adjustable by the adjustment pins to selectably dilate the valve.

In another aspect, the adjustment pins each comprise a tuning key. Each of the tuning keys has a rotatable knob coupled to a rotatable post via a gear set such that rotation of the knob rotates the post. The post is configured to receive a respective adjustment cord.

In still another aspect, the gear set comprises a worm gear and a mating pinion gear. The worm gear and pinion gear allow adjustment of the tensions on the adjustment cord which prevents rotation of the post in response to tension from the adjustment cord.

In yet another aspect, the mounting ring is formed of a pliable, elastomeric material for receiving sutures to secure a valve to the mounting ring. For example, a suturing needle can pierce through the mounting ring to suture the valve to the mounting ring.

In another aspect, the dilation device further includes a plurality of biasing mechanisms. Each of the biasing mechanisms is coupled to a respective adjustment cord between the adjustment pin and a valve mounted to the mounting ring. Each biasing mechanism biases the respective adjustment cord toward the dilating position, while allowing the adjustment cord to move toward the relaxed position against the biasing mechanism. This allows the dilation device to better simulate the conditions and operation of a mitral valve after being surgically repaired, such as during implantation of an annuloplasty ring. An annuloplasty ring restores the pathophysiologically dilated annulus to a normal diameter (i.e., the ring reduces the diameter of the annulus). The use of a biasing mechanism allows the surgical repair being tested to reduce the diameter of the annulus after it has been dilated by the dilation device so that various surgical repairs and devices can be tested under accurate annular dilation states and under various amounts of dilation provided by the dilation device.

In another aspect, the biasing mechanisms comprise springs disposed on the adjustment cords.

Another embodiment disclosed herein is directed to a system for modeling mitral regurgitation in a mitral valve using the dilation device having adjustment pins. In one embodiment, the system includes the dilation device having adjustment pins, and a heart simulator. The heart simulator includes a housing for mounting the dilation device at a location corresponding to a mitral valve of a heart; and a pump for directing fluid through the housing such that the fluid passes through a valve mounted to the dilation device.

Another embodiment disclosed herein is a method for modeling mitral regurgitation in a mitral valve using the dilation device having adjustment pins. The method includes providing the dilation device having adjustment pins. Each adjustment pin is coupled to a first end of a respective adjustment cord, such as by winding the first end around a post of the adjustment pin. A valve having a valve annulus is secured to the mounting ring such that valve is disposed within the ring aperture and the plate aperture. A second end of each adjustment cord is attached to the valve annulus of the valve at spaced apart locations of the valve annulus. A posterior region of the valve annulus is dilated by adjusting one or more of the adjustment pins.

In another aspect of the method, the adjustment cords comprise sutures, and attaching the second end of each adjustment cord to the valve annulus includes directing the sutures through the valve annulus.

In yet another aspect of the method, during dilation of the posterior region of the valve annulus, an anterior region of the annulus does not dilate substantially.

In still another aspect of the method, the valve is secured to the mounting ring using a plurality of sutures directed through the valve annulus and the mounting ring.

In another aspect of the method, the dilation device with the valve secured thereto is mounted within a heart simulator, and fluid is directed fluid through the simulator such that the fluid passes through the valve mounted to the dilation device to simulate operation of the valve.

In still another aspect of the method, the adjustment pins are adjusted to sequentially increase the amount of dilation of the valve annulus to analyze mitral regurgitation.

Additional aspects and features of the present invention will become apparent from consideration of the following description taken in conjunction with the accompanying drawings.

BRIEF DESCRIPTION OF THE DRAWINGS

The drawings illustrate exemplary embodiments of the invention, in which:

FIG. 7 is a table of hemodynamic parameters for the following states: baseline, pre-threshold dilation, and maximum dilation post-threshold.

DETAILED DESCRIPTION OF THE EXEMPLARY EMBODIMENTS

Figure 1A:
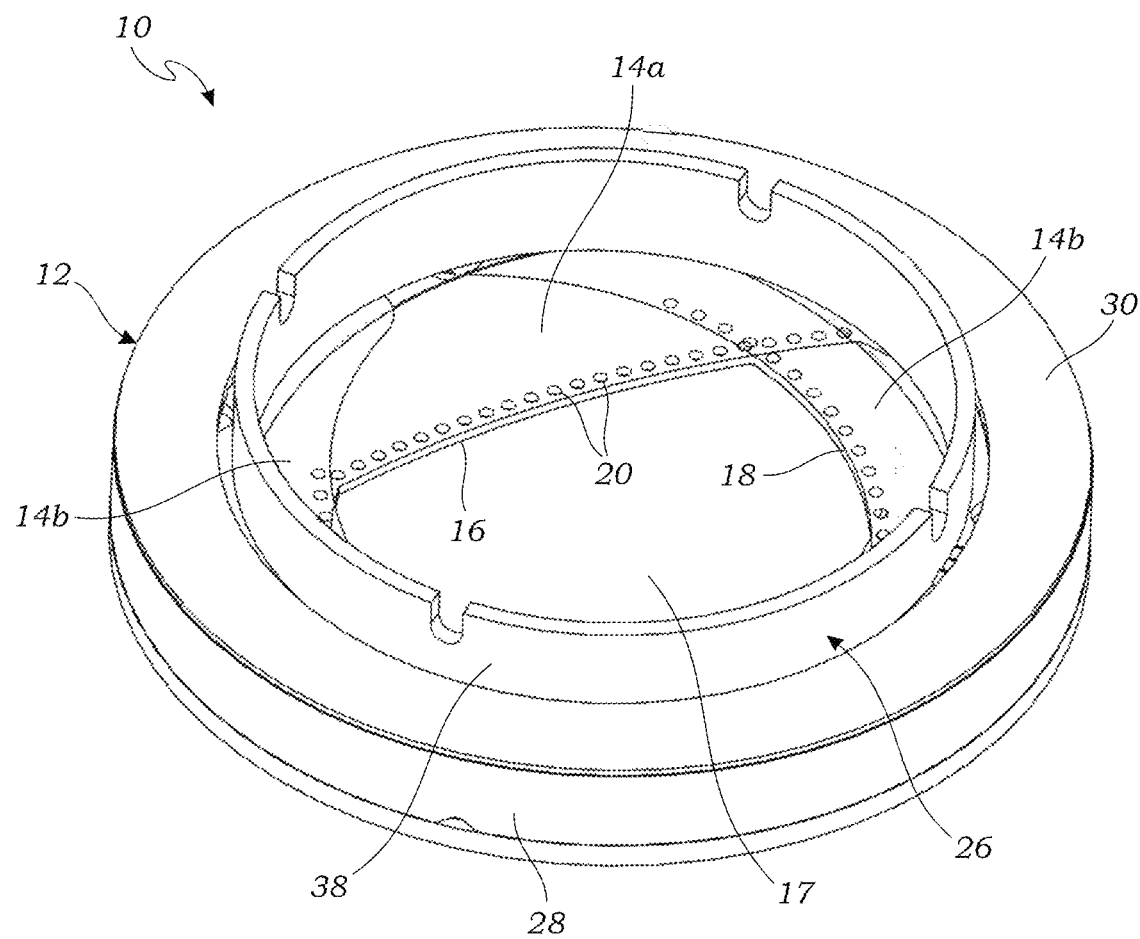
FIG. 1A is a perspective view of an exemplary embodiment of a dilation device.
Figure 1B:
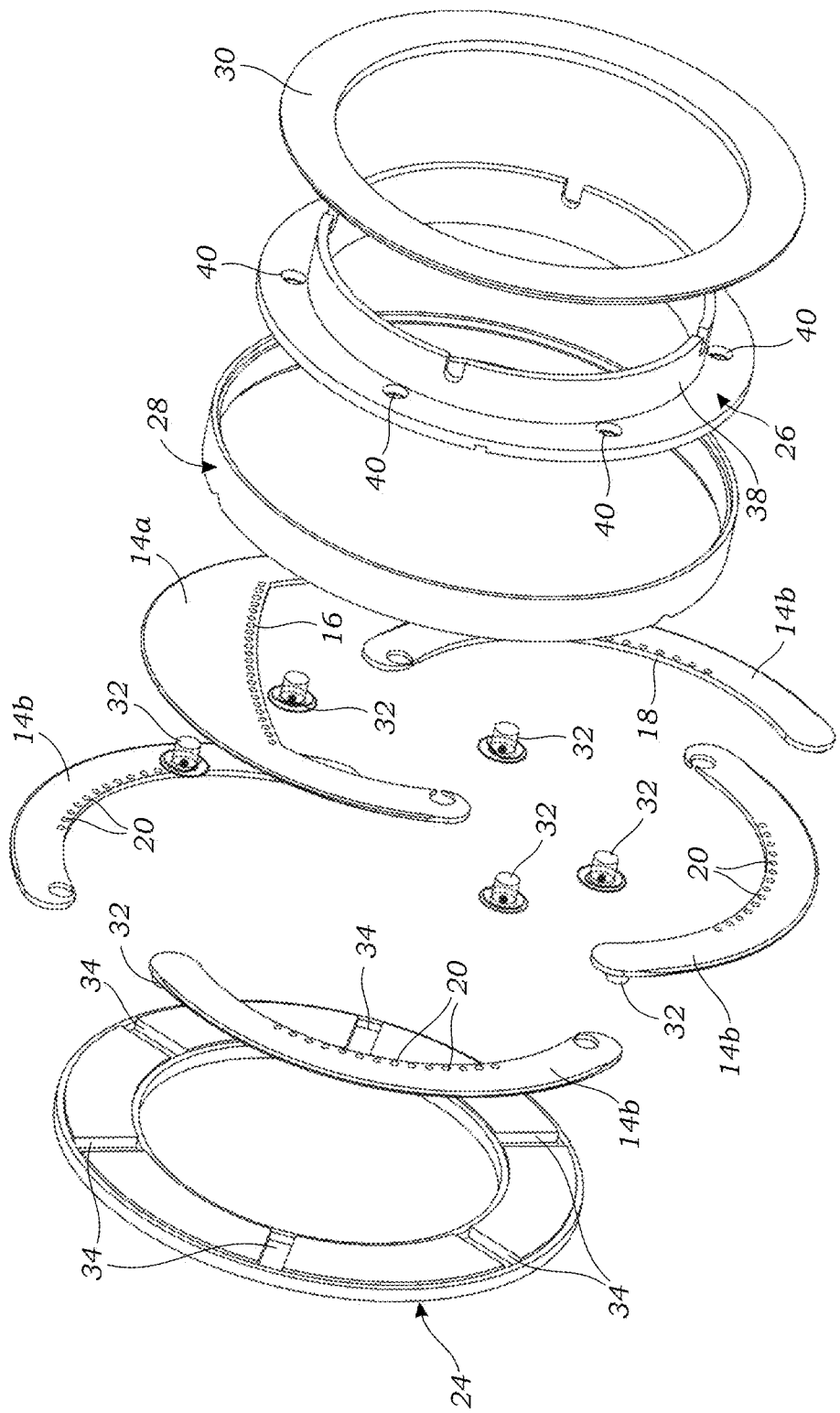
FIG. 1B is an exploded view of the dilation device of FIG. 1A.
Figure 1C:
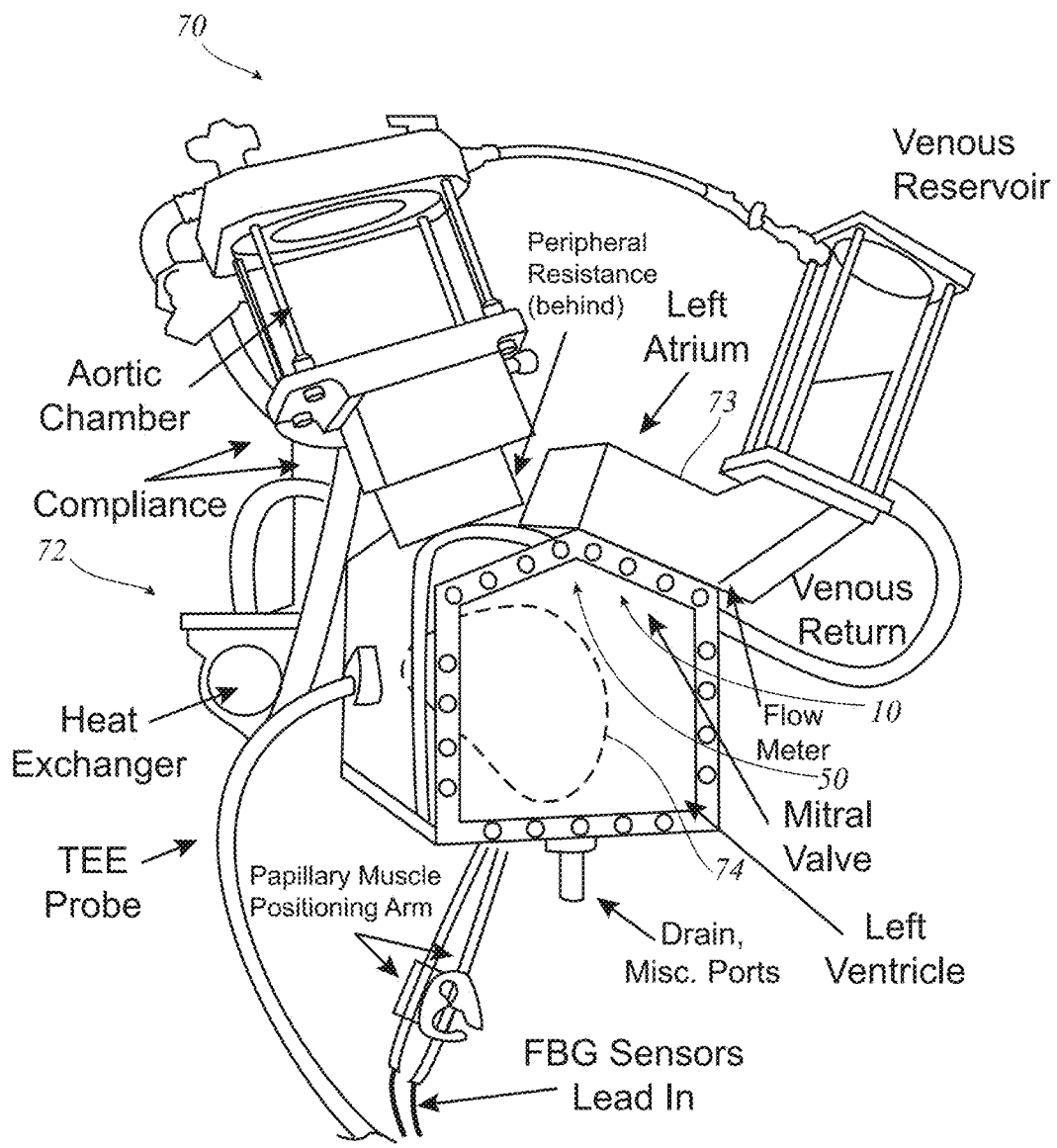
FIG. 1C shows an exemplary embodiment of a left heart simulator.

Referring to the drawings, FIGS. 1A and 1B show an exemplary embodiment of a valve dilation device 10 for selectively dilating a valve mounted to the dilation device 10. The dilation device 10 is inspired by an iris, and is configured to selectively dilate the posterior mitral valve annulus 52a (see FIGS. 2A and 2B) of a valve 50 mounted to the dilation device. The dilation device 10 may be configured to dilate the posterior annulus 52a of the valve 50 with negligible dilation of the anterior annulus 52b, or a smaller amount of dilation of the posterior annulus 52b. FIG. 1C shows an exemplary system 70 for testing a mitral valve 50, such as modeling mitral regurgitation in a mitral valve 50, and/or testing surgical procedures and repair devices for treating mitral regurgitation. The system 70 includes a left heart simulator 72 into which the dilation device 10 and valve 50 may be installed, e.g., to model mitral valve dilation, mitral regurgitation or other disease, and/or repair procedures and devices for the valve 50, as described elsewhere herein.

Figures 2A, 2B:
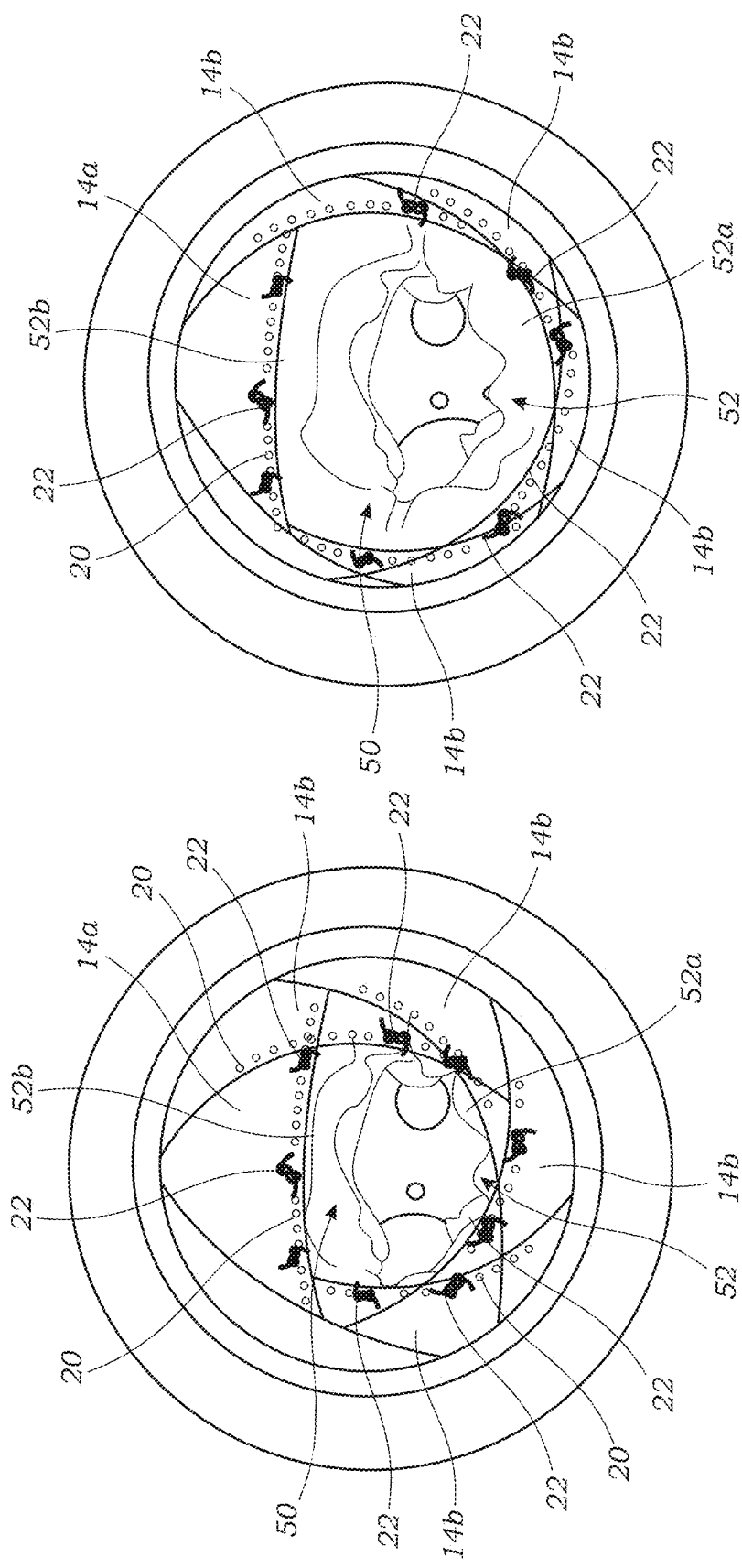
FIGS. 2A and 2B show a porcine valve sewn into the dilation device of FIGS. 1A and 1B in its native state (FIG. 2A) and a dilated state (FIG. 2B). As the pivot plate is turned, the overlapping blades rotate outwardly and open the aperture to stretch the annulus into a dilated configuration. The posterior section of the annulus is selectively dilated to mimic in vivo mitral valve dilation.

As best shown in FIGS. 1A and 1B, in one embodiment, the dilation device 10 includes a housing 12 carrying a plurality of blades 14 surrounding a central aperture 17 sized to receive a valve 50. The arrangement of the plurality of blades 14 is similar to the blades of an iris diaphragm which dilate and constrict to vary the size of an aperture (also referred to as a pupil) in the middle of the blades of the iris. The plurality of blades 14 include an anterior blade 14a defining a substantially straight inner edge 16, and a plurality of posterior blades 14b (the illustrated embodiment includes 4 posterior blades 14b) defining a curved inner edge 18, to which a valve 50 may be mounted, e.g., as shown in FIGS. 2A and 2B. The inner edges 16 and 18 of the blades 14 may include holes 20 or perforations 20 sized to receive sutures 22, or other fastening devices, to secure an annulus 52 of a valve 50 to the dilation device.

The blades 14 of the dilation device 10 may be 3D-printed, e.g., using cyanate ester or other strong and/or rigid plastic that allows for the extremely thin (e.g., about 0.62 mm or less) blades 14 so that the assembled dilation device 10 is thin enough to fit into a simulator, such as the left heart simulator 72 (see FIG. 1C). Alternatively, one or more of the blades 14 may be formed of a flexible material, such as an elastomer polymer or other suitable material, which allows the anterior blade 14b and posterior blades 14a to flex laterally to allow a mitral valve 50 mounted in the dilation device 10 to exhibit substantially natural motion during a cardiac cycle.

With continued reference to FIG. 1B, the housing 12 includes a base plate 24, a pivot plate 26, a spacer 28, and a top plate 30, each having a similar annular shape such that the components may be permanently attached together to form the housing 12. The blades 14 may include one or more pins 32 or other connectors 32 that may be received in holes, slots and/or other corresponding connectors in the base plate 24 and the pivot plate 26 to sandwich the blades 14 therebetween. Consequently, the base plate 24 and top plate 30 are stationary while the pivot plate 26 is movable, e.g., rotatable around a perimeter of the housing 12, to move the blades 14 between relaxed and dilated positions, as described elsewhere herein.

In an exemplary method, a high-resolution 3D printer (e.g., Carbon M2 Printer; Redwood City, CA) may be utilized to manufacture the components of the housing 12. This enable such components of the housing 12 to be made with a large range of material properties, complex geometries, and features as small as 0.2 mm. To accurately model mitral annular dilation, the dilation device 10 may mimic the D-shape of a natural annulus 52 of a mitral valve 50 while dilating the posterior annulus 52a with negligible dilation, or a smaller dilation, of the anterior annulus 52b.

Figure 1D:
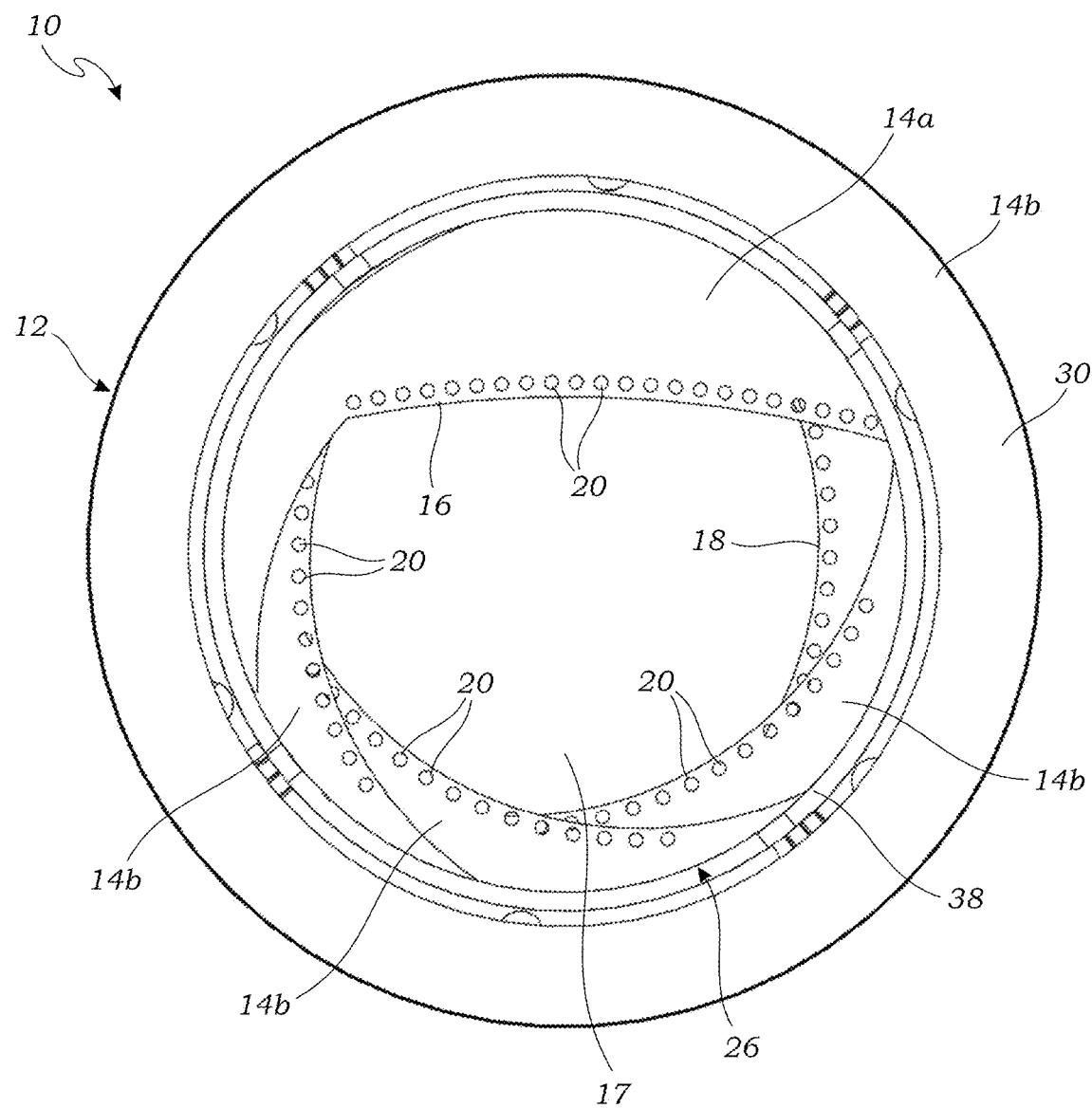
FIG. 1D shows the dilation device of FIG. 1A in a relaxed position.
Figure 1E:
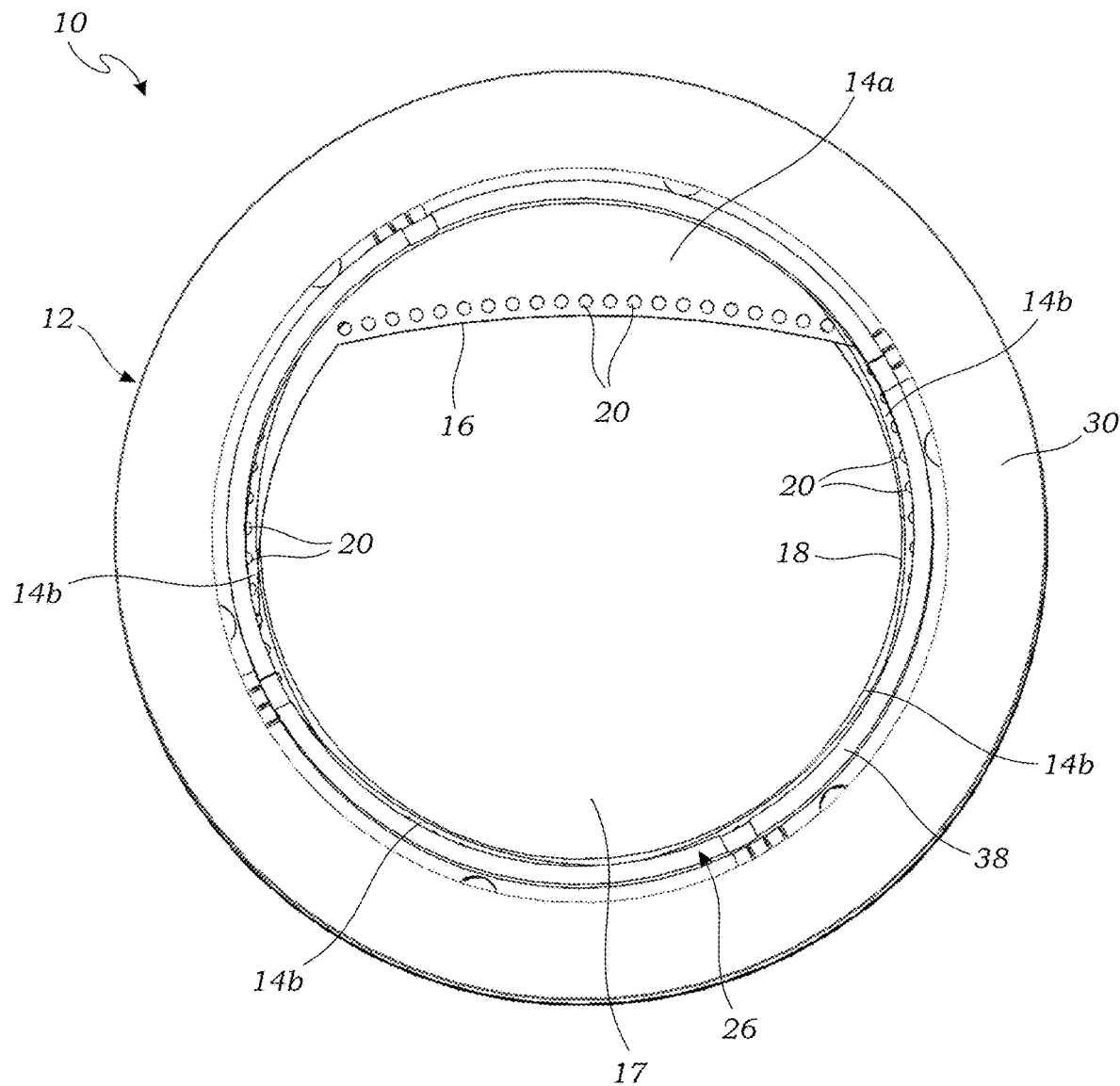
FIG. 1E shows the dilation device of FIG. 1A in a dilating position.

FIGS. 1D and 1E illustrate how the blades 14 of the dilation device 10 are actuatable between a relaxed position shown in FIG. 1D and a dilating position shown in FIG. 1E. Rotation of the pivot plate 26 in a first direction (e.g., clockwise) causes the blades 14 to move outwardly and rotation of the pivot plate 26 in a second direction opposite the first direction (e.g., counter-clockwise) causes the blades 14 to move inwardly. In other embodiments, the dilation device 10 is configured such that only the posterior blades 14b move to the dilating position, while the anterior blade 14a does not move substantially, or only moves a smaller amount (i.e., the anterior blade 14a remains substantially in the relaxed position, or non-dilating position).

FIGS. 2A and 2B show the dilation device 10 of FIGS. 1A and 1B with a porcine mitral valve 50 mounted thereto in its native state (FIG. 2A) and in a dilated state (FIG. 2B). In order to achieve a D-shaped aperture that selectively dilates the posterior annulus 52a of the valve 50, the anterior section 52b of the valve annulus 52 is sewn to the straight inner edge 16 of the anterior blade 14a and thus the anterior annulus 52b does not dilate substantially, or dilates a smaller amount than the posterior annulus 52a, upon actuating the dilation device 10 from the relaxed position (FIG. 2A) to the dilating position (FIG. 2B). The posterior section 52a of the annulus 50 is sewn to the other four blades 14b, which open to the dilating position (as shown in FIG. 2B) to dilate the posterior annulus 52a.

In an exemplary embodiment, the blades 14 of the device 10 may be printed using cyanate ester, a strong and rigid plastic that allows for the blades 14 to be extremely thin (0.62 mm) so that the dilation device 10 can fit in the left heart simulator 72. Additionally, small perforations 20 may be included along the inner edge border of the anterior blades 14b to facilitate suturing to the posterior valve annulus 52a.

The blades 14 may also include one or more pins 32 on each of their ends (a first end and a second end), e.g., one pointed up and one pointed down, that fit into the base plate 24 and pivot plate 26, respectively. For example, each of the posterior blades 14b may include a pin 32 on a first end rotatably coupled to the pivot plate 26 and a pin 32 on a second end slidably coupled to a respective slot 34 in the base plate 24, such that rotation of the pivot plate 26 causes the second end to move radially inward and outward when the pivot plate 26 rotates, thereby causing posterior blades 14b to rotate inwardly and outwardly relative to the housing 12 between relaxed and dilating positions.

The pivot plate 26 includes an annular base 36 and a cylindrical raised section 38 extending upward from the annular base 36. The annular base 36 has a plurality of holes 40 which receive the pins 32 of the blades 14. The pins 32 are rotatable within the holes 40 to allow the blades 14 to pivot relative to the pivot plate 26.

The base plate 24 may be formed from elastic polyurethane or other rubbery material to create a hemodynamic seal around the valve 50 and also facilitate easy sewing. The base plate 24 has a plurality of slots 34 for slidably receiving the pins 30 of the blades 14. The spacer 28 separates the base plate 24 of the housing 12 from the stationary top plate 30 which surrounds the raised section 38 of the pivot plate 26. The spacer may be a cyanate ester ring, or other suitable material. The spacer 28 allows pressure to be applied to the top plate 30 (transmitted to the spacer 28 and to the base plate 24) in order to establish a seal between the left ventricular chamber of the heart simulator 72 and the base plate 24, while not preventing the pivot plate 26 from being rotated to actuate the dilation device 10 between the relaxed position and the dilated position.

Referring now to FIG. 1C, the system 70 for testing a mitral valve 50, such as modeling mitral regurgitation in a mitral valve, and/or testing surgical procedures and repair devices for treating mitral regurgitation, is illustrated. The system 70 includes a left heart simulator 72 into which the dilation device 10 with the valve 50 mounted therein are installed at a location corresponding to a mitral valve of a heart, such that the pump of the heart simulator 72 directs fluid through the housing such that the fluid passes from the left atrium 73, through the valve 50 mounted to the dilation device 10, and into the left ventricle 74. The system 70 is instrumented with pressure sensors and flow sensors to measure and record ventricular, aortic, and left atrial pressures, and flow rates through the aortic and mitral locations during operation of the simulator 72. Accordingly, the system 70 can then be used to test the valve 50 in a native state (i.e., prior to repair) with the asymmetric annular dilation state ex vivo and with a continuous dilation profile. In other words, the valve 50 can be tested on the system 70 with the valve 50 dilated in small increments (or continuously) by the dilation device 10 while hemodynamic and force data are taken at each of the increments. The valve 50 can also be tested after a repair procedure using the system 70 and dilation device 10, such as implantation of an annuloplasty ring. Again, the valve 50 can be tested with varying amounts of dilation as applied by the dilation device 10.

Methods of using the dilation device 10 and/or the system 70, will now be described. In one embodiment, the method includes providing the dilation device 10, as described herein. A valve 50 is installed on the dilation device 10. For instance, an annulus 52 of the valve 50 (e.g., a mitral valve 50) is secured to the blades 14 of the dilation device 10. More specifically, the anterior annulus 52b is secured to the anterior blade 14a by installing one or more sutures 22 through the perforations 20 along the inner edge 16 of the anterior blade 14 and through the anterior annulus 52b. Similarly, the posterior annulus 52a is secured to the posterior blades 14b by installing one or more sutures 22 through the perforations 20 along the inner edge 18 of each of the posterior blades 14b and through the posterior annulus 52a. Then, in one embodiment of the methods, the dilation device 10 is actuated to cause the posterior blades 14b to dilate the posterior annulus 52a from a native state to a dilated state. More specifically, the pivot plate 26 is rotated which causes the posterior blades 14b to move outwardly from the relaxed position to a first dilating position. The pivot plate 26 may then be further rotated which causes the posterior blades 14b to move further outwardly from the relaxed position to a second dilating position, which dilates the valve 50 more than the first dilating position. The pivot plate 26 may be moved incrementally, or continuously, to move the posterior blades 14b to various dilating positions to incrementally, or continuously, vary the amount of the dilation of the valve 50. In another aspect, the rotation of the pivot plate 26 causes the posterior blades 14b to dilate with negligible dilation, or a smaller amount of dilation, of the anterior blades 14a, and thus, negligible dilation, or a smaller amount of dilation, of the anterior annulus 52b. For instance, negligible dilation of the anterior annulus 52b means less than 20% of the dilation of the posterior annulus 52a. Alternatively, during actuation, the dilation device 10 dilates the anterior annulus 52b (and anterior blade 14a) a smaller amount than the dilation of the posterior annulus 52a (and posterior blade 14b), such as less than 30%, or less than 40%, or less than 50%, of the dilation of the posterior annulus 52a.

In another embodiment of the methods disclosed herein, a surgical repair is performed on the valve 50 and the valve 50 is installed on dilation device 10, as described herein. The dilation device 10 is then actuated as described herein to vary the amount of dilation of the valve 50.

In another embodiment of the methods disclosed herein, the dilation device 10 having a valve 50 installed thereon is mounted on the heart simulator 72. The heart simulator 72 is operated to direct fluid through the valve 50 mounted on the heart simulator 72 to simulate operation of the valve 50. The dilation device 10 is then actuated as described herein to vary the amount of dilation of the valve 50. The operation of the valve 50 is monitored at each of the dilation settings of the dilation device 10 using the pressure sensors and flow sensors of the heart simulator 72 to measure and record ventricular, aortic, and left atrial pressures, and flow rates through the aortic and mitral locations during operation of the simulator. This process can be repeated for the valve 50 in its native state, and after a surgical repair, as described above. In addition, the process may also be repeated for different surgical repairs and different repair devices to compare the effectiveness of the repairs and devices (e.g., different annuloplasty ring designs) and for different amounts of valve dilation.

Figure 8:
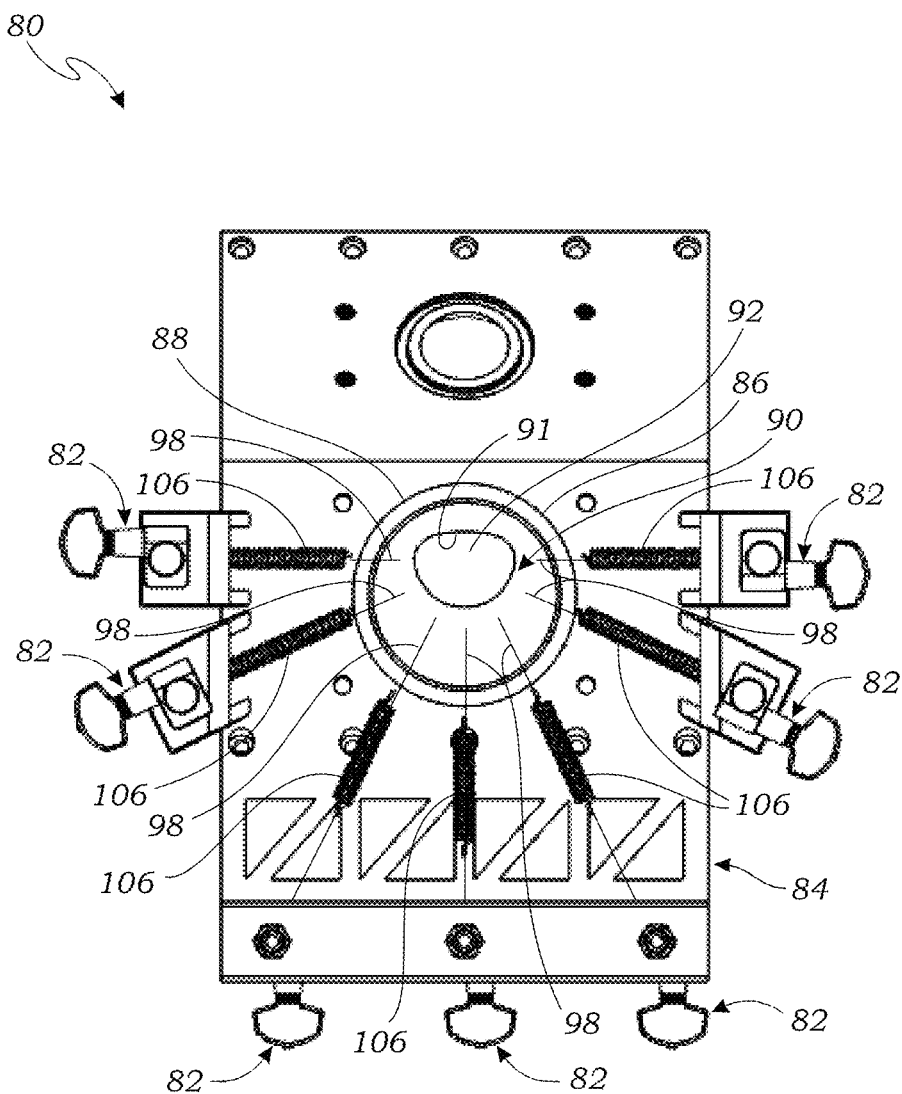
FIG. 8 is top view of another embodiment of a dilation device.
Figure 9:
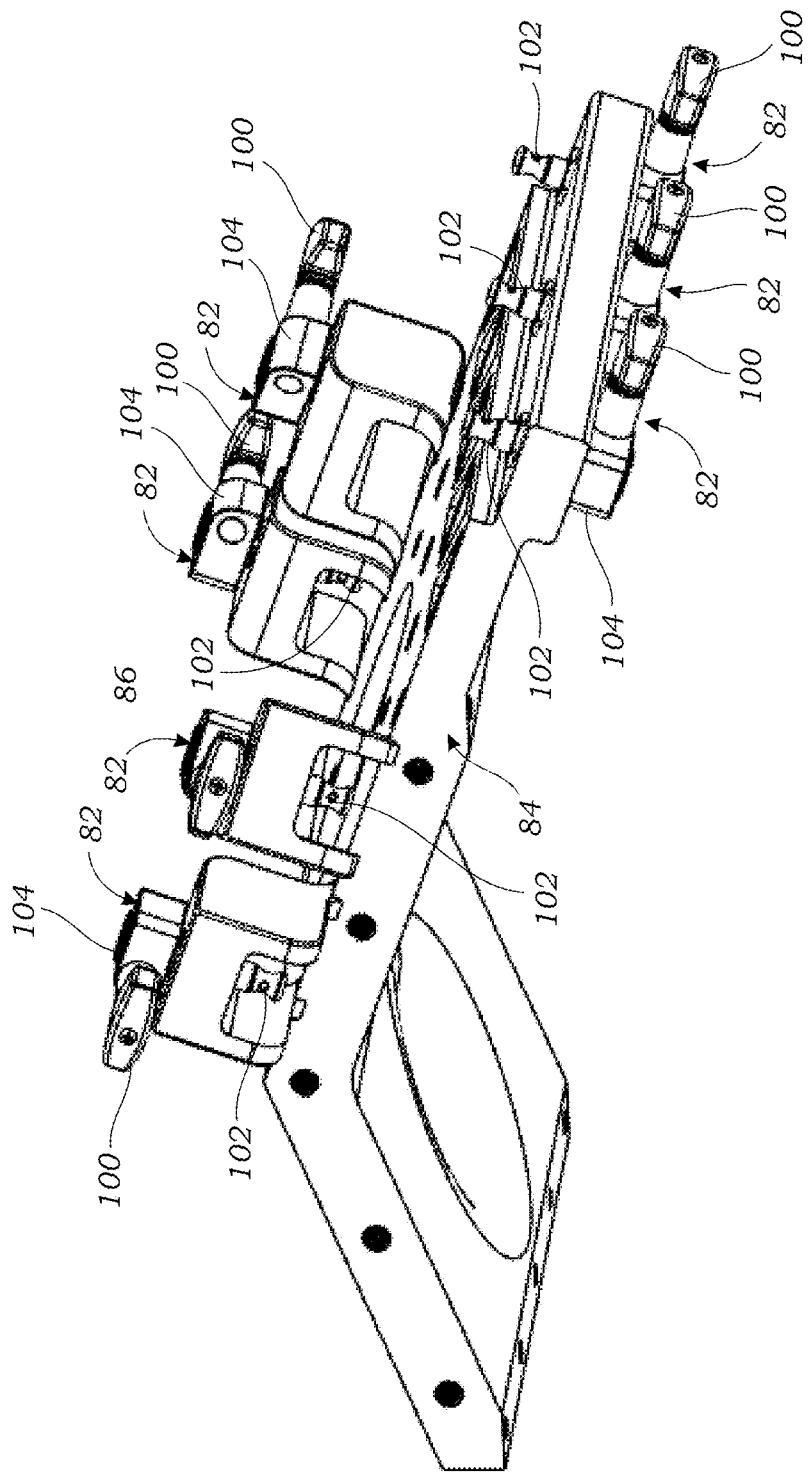
FIG. 9 is a side, perspective view of the dilation device of FIG. 8.

Turning to FIGS. 8-13, another embodiment of a dilation device 80 to selectively dilate the posterior annulus 52a of an explanted mitral valve 50 utilizes adjustment pins 82 to selectively dilate a valve 50. The dilation device 80 can be used for the same uses and purposes as the dilation device 10 having dilating blades 14, as described above. Referring to FIGS. 8 and 9, the dilation device 80 includes a base plate 84 having a plate aperture 86 and a recess 88 surrounding the plate aperture 86.

Figure 10:
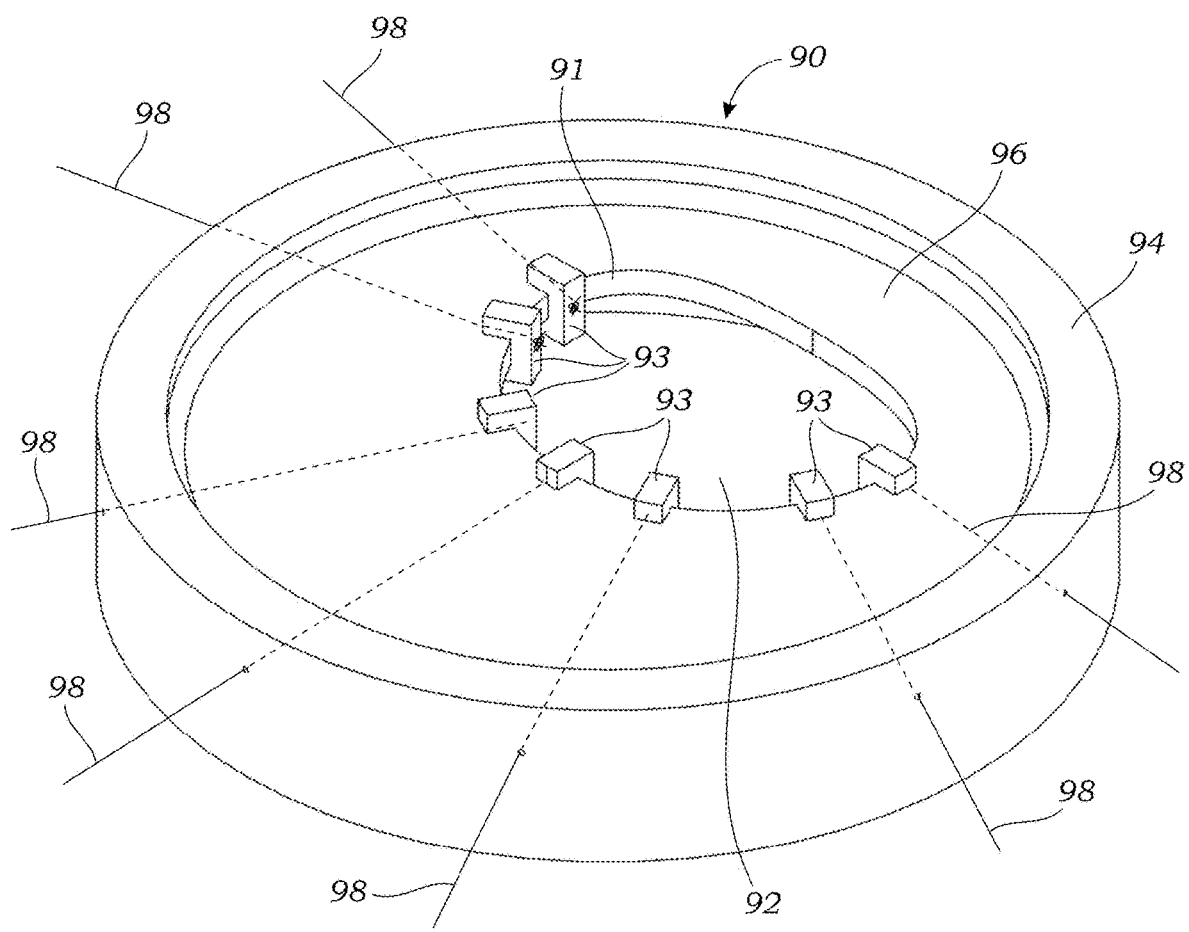
FIG. 10 is side, perspective view of the mounting ring of the dilation device of FIG. 8.
Figure 11:
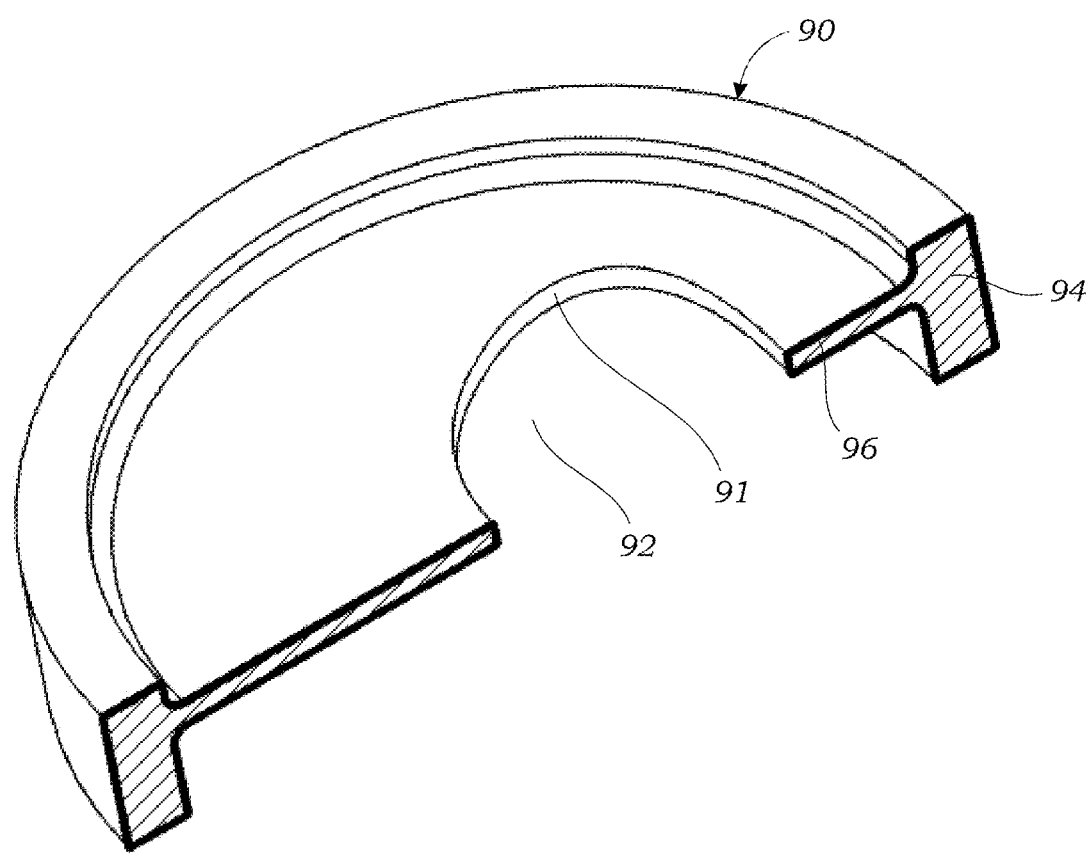
FIG. 11 is a side, perspective, sectional view of the mounting ring of FIG. 10.

A valve mounting ring 90 is mounted in the recess 88 of the base plate 84. The mounting ring 90 has a ring aperture 92 which forms an inner edge 91 of the mounting ring 90. The ring aperture 92 is aligned with the plate aperture 86 when the mounting ring 90 is installed on the base plate 84. The plurality of adjustment pins 82 are mounted on the base plate 84 and are angularly spaced around the mounting ring 90. The mounting ring 90 is removable from the base plate 84 such that it is easily replaceable. For example, a different mounting ring 90 can be used each time the valve 50 is changed during use of the dilation device 80. Turning to FIGS. 10 and 11, the mounting ring 90 has a circular shape, but may have any suitable shape to fit the recess and/or 88 and plate aperture 86. The mounting ring 90 has a thicker, outer annular edge 94 and a thinner, circular inner body 96 within the annular edge 94. The mounting ring 90 may be formed of a pliable, elastomeric material which is relatively easy to suture through such that a suturing needle can pierce through the inner body 96 of the mounting ring 90 to secure the valve 50 to the mounting ring 90. In an alternative embodiment, the mounting ring 90 may not have a uniform cross-section all around the entire ring 90, as depicted in the illustrated embodiment. Instead, the anterior section of the mounting ring 90 may be substantially thicker than the posterior section such that the anterior section is much stiffer than the posterior section, which prevents the dilation device 80 from dilating the anterior annulus 52*b*, or at least dilates the anterior annulus 52*b* less than the posterior annulus 52*a*.

Figure 12:
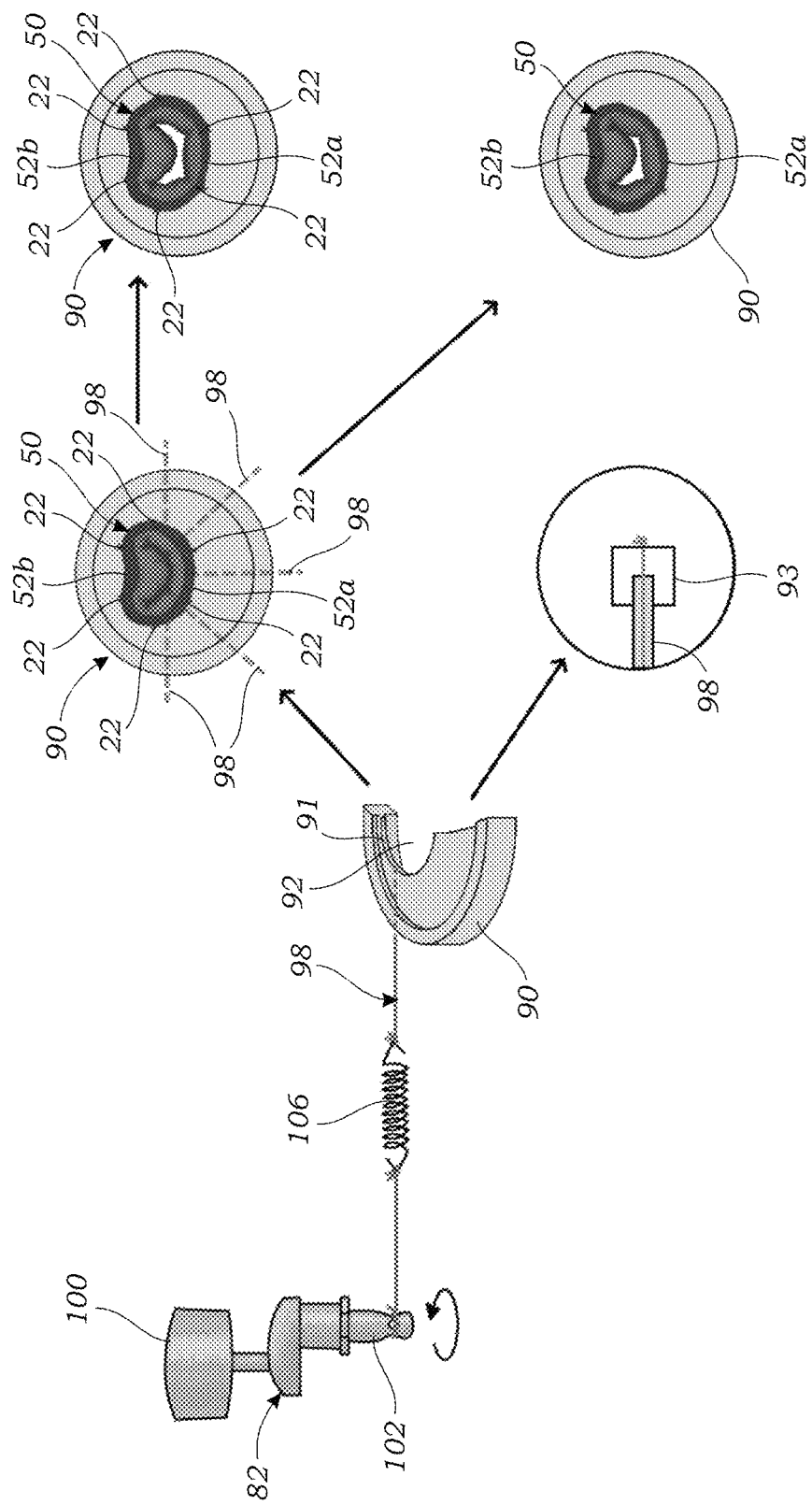
FIG. 12 is a schematic view of the dilation device of FIG. 8 showing an adjustment pin, adjustment cord and a valve mounted to the mounting ring in various states of dilation.

The illustrated embodiment of the dilation device 80 has seven (7) adjustment pins 82. The dilation device 80 may include more or fewer adjustment pins 82 as needed or desired to appropriately dilate a valve 50 mounted on the dilation device 80. The dilation device 80 has three (3) adjustment pins 82 disposed around the posterior annulus 52*a* of the valve 50, and two (2) adjustment pins 82 on each side of the posterior annulus 52*a* going up to the anterior most region of the posterior annulus 52*a*. The dilation device 80 does not have adjustment pins 82 disposed around the anterior annulus 52*b*, as the anterior annulus 52*b* is typically not dilated during use of the dilation device 80 during use as described herein. However, the dilation device 80 may also include adjustment pins 82 disposed around the anterior annulus 52*b*, as well, in order to dilate the anterior annulus 52*b*. Each of the adjustment pins 84 is configured to receive a respective adjustment cord 98 (see FIGS. 8, 10 and 12). The adjustment cords 98 are attachable to the posterior valve annulus 52 mounted on the mounting ring 90. The length and tension of the adjustment cords 98 are adjusted by the adjustment pins 82 which pull on the valve annulus 52 to selectively dilate the valve annulus 52. The adjustment cords 98 may be embedded in the mounting ring, as depicted in FIG. 12, such as by molding the mounting ring 90 with the adjustment cords 98 positioned in the mold. The adjustment cords 98 form a respective lumen in the mounting ring 90 through which the adjustment cords 98 extend (see FIG. 10). Alternatively, the adjustment cords 98 may lie on the top of the mounting ring 90. A first end of each adjustment cord 98 is coupled to a respective adjustment pin 82 by winding the first end around the post 102 of the adjustment pin 82. The second end of each adjustment cord 98 is attached to the inner edge 91 of the mounting ring at spaced apart locations of the inner edge 91. In one embodiment, the second ends of the adjustment cords 98 may be attached to the inner edge 91 by tying the second ends to the inner edge 91 or by tying a knot which is larger than the lumen through which the embedded adjustment cords 98 extend. In another embodiment, as depicted in FIG. 12, the second end of each adjustment cord 98 is attached to a clip 93 which clips onto the inner edge 91. Alternatively, the second end of each adjustment cord 98 may be directly attached to the posterior annulus 52*a* of the valve 50 at spaced apart locations of the valve annulus 52.

In the illustrated embodiment, each adjustment pin 82 comprises a tuning key, same or similar to a tuning key of a guitar. Each of the tuning keys has a rotatable knob 100 coupled to a rotatable post 102 via a gear set 104 such that rotation of the knob 100 rotates the post 102. Each of the adjustment cords 98 is coupled to a respective post 102 of one of the adjustment pins 82. The gear set 104 may include a worm gear and a mating pinion gear, or other suitable gear set for transferring the rotational movement of the knob 100 to rotation of the post 102. A gear set 104 including a worm gear and pinion gear has the advantage that it allows adjustment of the tension on the adjustment cord 98 while preventing rotation of the post 102 in response to tension from the adjustment cord 98.

The dilation device 80 also has a plurality of biasing mechanisms 106. In the illustrated embodiment, the biasing mechanisms 106 are springs 106. Each of the biasing mechanisms 106 is coupled to a respective adjustment cord 98 between the adjustment pin 82 and the connection to the valve annulus 52. Each biasing mechanism 106 biases the respective adjustment cord 98 toward the dilating position, while allowing the adjustment cord 98 to move toward the relaxed position against the biasing mechanism 106. This allows the dilation device 80 to better simulate the conditions and operation of a mitral valve 50 after being surgically repaired, such as during implantation of an annuloplasty ring. The biasing mechanism 106 allows the surgical repair being tested to reduce the diameter of the annulus 52 after it has been dilated by the dilation device 80 so that various surgical repairs and devices can be tested under accurate annular dilation states and under various amounts of dilation provided by the dilation device.

Figure 13:
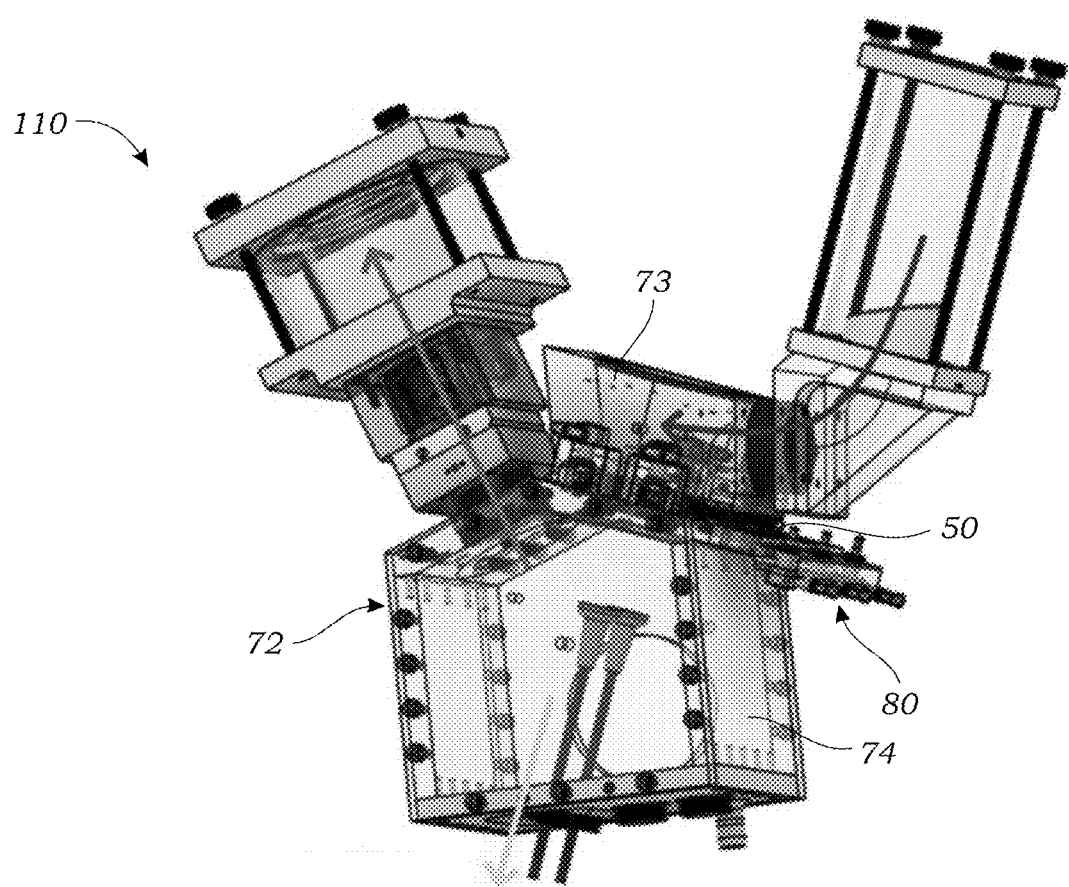
FIG. 13 is a perspective view of a left heart simulator with the dilation device of FIG. 8 installed on the simulator.

Referring to FIG. 13, a system 110 for testing a mitral valve 50, such as modeling mitral regurgitation in a mitral valve, and/or testing surgical procedures and repair devices for treating mitral regurgitation, is illustrated. The system 110 includes the dilation device 80 having adjustment pins 82, and a heart simulator 72, same or similar to the heart simulator 72 described above. The dilation device 80 is mounted in a housing of the heart simulator 72 at a location corresponding to a mitral valve of a heart, such that the pump of the heart simulator directs fluid through the housing such that the fluid passes through the valve 50 mounted to the dilation device 80.

The method of using the dilation device 80 for modeling mitral regurgitation in a mitral valve is similar to the method of using the dilation device 10. Referring to FIG. 12, a valve 50 is installed on the dilation device 80. The valve 50 is secured to the mounting ring 90 such that valve 50 is disposed within the ring aperture 92 and the plate aperture 86. The annulus 52 of the valve 50 (e.g., a mitral valve 50) is secured to the mounting ring 90 by installing one or more sutures 22 through the inner body 96 of the mounting ring 90 and through the valve annulus 52. Each adjustment pin 82 is coupled to a first end of a respective adjustment cord 98, by winding the first end around the post 102 of the adjustment pin 82. The second end of each adjustment cord 98 is attached to the inner edge 91 of the mounting ring 90, or to directly to the posterior annulus 52*a* of the valve 50 at spaced apart locations of the valve annulus 52, as described above. The valve annulus 52 is dilated by adjusting one or more of the adjustment pins 82 to increase the tension in the respective adjustment cord(s) 98. The adjustment pins 82 may be adjusted to incrementally, or continuously, adjust the tension on the adjustment cord(s) 98 to incrementally, or continuously, vary the amount of the dilation of the valve 50. The adjustment of the adjusting pins 82 dilate the posterior annulus 52*a* with negligible dilation, or a smaller amount of dilation, of the anterior annulus 52*b*. For instance, negligible dilation of the anterior annulus 52*b* means less than 20% of the dilation of the posterior annulus 52*a*. Alternatively, during actuation, the dilation device 80 dilates the anterior annulus 52*b* a smaller amount than the dilation of the posterior annulus 52*a*, such as less than 30%, or less than 40%, or less than 50%, of the dilation of the posterior annulus 52*a*.

In another embodiment of the methods disclosed herein, a surgical repair is performed on the valve 50 and the valve 50 is installed on dilation device 80, as described above. The dilation device 80 is then actuated as described above to vary the amount of dilation of the valve 50.

In another embodiment of the method, the dilation device 80 with the valve 50 secured thereto is mounted on the heart simulator 72. The heart simulator 72 is operated to direct fluid through the valve 50 mounted on the simulator 70 to simulate operation of the valve 50. The dilation device 80 is then actuated as described herein to vary the amount of dilation of the valve 50. The operation of the valve 50 is monitored at each of the dilation settings of the dilation device 80 using the pressure sensors and flow sensors of the heart simulator 72 to measure and record ventricular, aortic, and left atrial pressures, and flow rates through the aortic and mitral locations during operation of the simulator. This process can be repeated for the valve 50 in its native state, and after a surgical repair, as described above. In addition, the process may also be repeated for different surgical repairs and different repair devices to compare the effectiveness of the repairs and devices (e.g., different annuloplasty ring designs) and for different amounts of valve dilation.

Experimental Examples

The following examples, and corresponding figures demonstrate the use of a system 70, left heart simulator 72 and dilation device 10 constructed in accordance with the descriptions herein to test a mitral valve (porcine) in a native state, a dilated state, and after a surgical repair with an annuloplasty ring.

Valve Preparation

Porcine hearts (n=3) were locally obtained, and the mitral valves 50 were carefully excised to preserve the annulus 52, leaflets, and chordae. Only valves 50 sized 30-34 mm were used to allow for sufficient dilation with the dilation device 10, and hearts with aberrant papillary muscle anatomy were excluded. To attach the valve 50 to the dilation device 10, eight interrupted 2-0 braided polyester sutures 22 were used (see FIGS. 2A and 2B). Care was taken to ensure that the anterior section 52*b* of the annulus 52 was sewn to the straight inner edge 16 of the anterior blade 14*a*, and that no suture ties 22 restricted movement of the overlapping blades 14. In order to seal the valve 50 to the base plate 24 and thus seal the juncture between the left atrium and LV sections of the left heart simulator 72, a continuous 2-0 polypropylene suture 22 tacked the elastic polyurethane backing of the base plate 24 to a cuff of left atrium tissue. For proper papillary muscle positioning, each muscle was sewn to custom molded silicone holders using four interrupted, pledgeted, 2-0 braided polyester horizontal mattress sutures each. These holders were then affixed to carbon fiber rods within the left ventricular chamber of the heart simulator 72 and positioned to mimic in vivo placement.

Left Heart Simulator

FIG. 1C shows an exemplary embodiment of the left heart simulator 72 into which the dilation device 10 and valve 50 were secured. As shown, the simulator 72 includes a left heart chamber, e.g., which may be 3D-printed or otherwise formed, and mounted to a pulsatile linear piston pump (e.g., the ViVitro Superpump, ViVitro Labs, Victoria, BC, Canada) with the ability to generate physiologic conditions. The dilation device 10 and valve 50 were secured at a location in the simulator 72 corresponding to the location of the mitral valve, i.e., between chambers corresponding to the left atrium and the left ventricle. An actuator was coupled to the pivot plate 26 to rotate or otherwise move the pivot plate 26 and, consequently, rotate or otherwise direct the posterior blades 14*b* outwardly to from the relaxed position (see FIG. 2A) to the dilating position (see FIG. 2B) to dilate the valve 50 at a desired rate, as described elsewhere herein.

During operation of the simulator 72, ventricular, aortic, and left atrial pressures were recorded using pressure transducers (e.g., from Utah Medical Products Inc., Midvale, Utah), and flow through the aortic and mitral locations was recorded using electromagnetic flow probes (e.g., from Carolina Medical Electronics, East Bend, North Carolina).

In order to ensure transduction of the flow meters, 0.9% normal saline was used as the test fluid and maintained at 37° C. physiologic testing condition. The pump was set to generate an effective stroke volume of 70 mL/beat at 70 bpm, and was programmed to comply with ISO 5840 standards for in vitro valve testing. Cardiac output was held at 5 L/min while peripheral resistance and compliance were titrated to produce a physiologic pressure waveform (systolic 120 mmHg, diastolic 80 mmHg).

The valve 50 was dilated in small increments while hemodynamic and force data was collected. For each stage of dilation, ten cycles of hemodynamic data were collected and averaged. Videos were also obtained at each stage with a high-speed digital camera (e.g., Chronos 1.4, Kron Technologies, Burnaby, BC, Canada) at an en face perspective of the mitral valve, and then processed using ImageJ (Bethesda, Maryland) to quantify the percent annular dilation. Aortic, ventricular, and atrial pressure tracings as well as flow tracings were recorded using the ViVitest software and data acquisition system. MR at each stage was calculated using the flow measurements. A preliminary annuloplasty ring test was performed to explore the use of the dilation device 10 to test annuloplasty ring design; and an additional porcine valve was tested in a native state, dilated state, and then repaired with a full, rigid annuloplasty ring (e.g., Carpentier-Edwards Physio II, Edwards, Irvine, CA).

Chordae Tendineae Force Measurement

Chordal forces were measured using Fiber Bragg Grating (FBG) optical strain gauge sensors (e.g., DTG-LBL-1550 125 μm FBGS International, Belgium) with a sensitivity of approximately 0.1μ strain. The force measurement method and strain gauge calibration has been described previously. FBGs have a low mass and a thin profile of 0.75 mm after encasing in a wire spring and water-resistant tubing. Thus, multiple chordae could be instrumented without disrupting the hemodynamics and structural integrity of the valve. The strain gauges were manufactured by threading the FBG through a protective coil sheath that served as a mechanism for suture attachment and increased the durability of the sensor by supporting flexibility without cracking. Each sensor was individually calibrated using an Instron Microtester (Norwood, MA) with a 10N load cell. The sensor was subjected to known tensile loads (0N to 2N -representative of the forces during experimentation) while strain data was collected using an optical interrogator with dedicated software (e.g., Micron Optics si255 with ENLIGHT, Micron Optics, Atlanta, Georgia) at a sampling frequency of 1000 Hz. A least squares regression was used to correlate the FBG strain data to the Instron load data, specific to each sensor. For each valve, multiple native chordae (n=4-5) were instrumented with FBG gauges. Care was taken to capture a variety of locations—including primary and secondary chordae in both posterior and anterior positions. The sensors were fixed to native chordae using double-armed polytetrafluoroethylene (PTFE) suture (e.g., Gore-Tex® Suture, WL Gore & Associates Inc., Flagstaff, Arizona) sewn proximally and distally to the FBG gratings.

Once attached, the segment of chordae between the suture attachment points was cut, allowing the force on the chordae to transmit entirely through the FBG sensor while the length of the instrumented chordae remained constant. Maximum chordal forces were calculated as the average force during systole.

Statistical Analysis

Statistical significance was set at P<0.05 for all tests. Continuous variables are reported as mean±standard deviation unless otherwise specified. For the hemodynamic data, non-parametric Friedman tests were used to compare continuous variables between groups. This test accounts for non-normally distributed forces and for the fact that the experimental method included multiple data collection stages for each valve 50. The non-parametric Friedman test reports one significance value for multiple treatment groups to identify significance in results correlated with changes in annular dilation, and then individual pairwise comparisons were performed between datasets of interests. Least-squares regression models were used for fitting mitral regurgitation and chordal force data, with p-values calculated using the F-test.

Results

The dilation device 10 was successful in selectively dilating the posterior annulus 52a of the porcine mitral valve 50, which in turn enabled the analysis of dilation-induced MR. FIG.

3A shows the change in mitral regurgitant fraction versus percent annular dilation for a compilation of all valves 50 tested. To account for variations between valves 50, the change in regurgitant fraction is in reference to the regurgitation measured in the baseline state (corresponding to 0% annular dilation). As expected from previous literature, the data showed a threshold for the onset of MR as the percent annular dilation increased. Thus, operating under the assumption that prior to this threshold the slope of MR versus percent annular dilation would be negligible, a piecewise linear regression model was used to fit the data with the slope of the first section set to 0. The resulting piecewise function was: G=0 when d<25.6; G=2.5*d−64 when d≥25.6 ($R^2$=0.90, p<0.01), where d is the percent annular dilation and G is the regurgitant fraction increase from baseline. This represents a threshold value for the onset of MR at 25.6% annular dilation. For annular dilation greater than 25.6%, a 2.5% increase in regurgitant fraction was observed for every 1% increase in annular dilation.

Figure 3A:
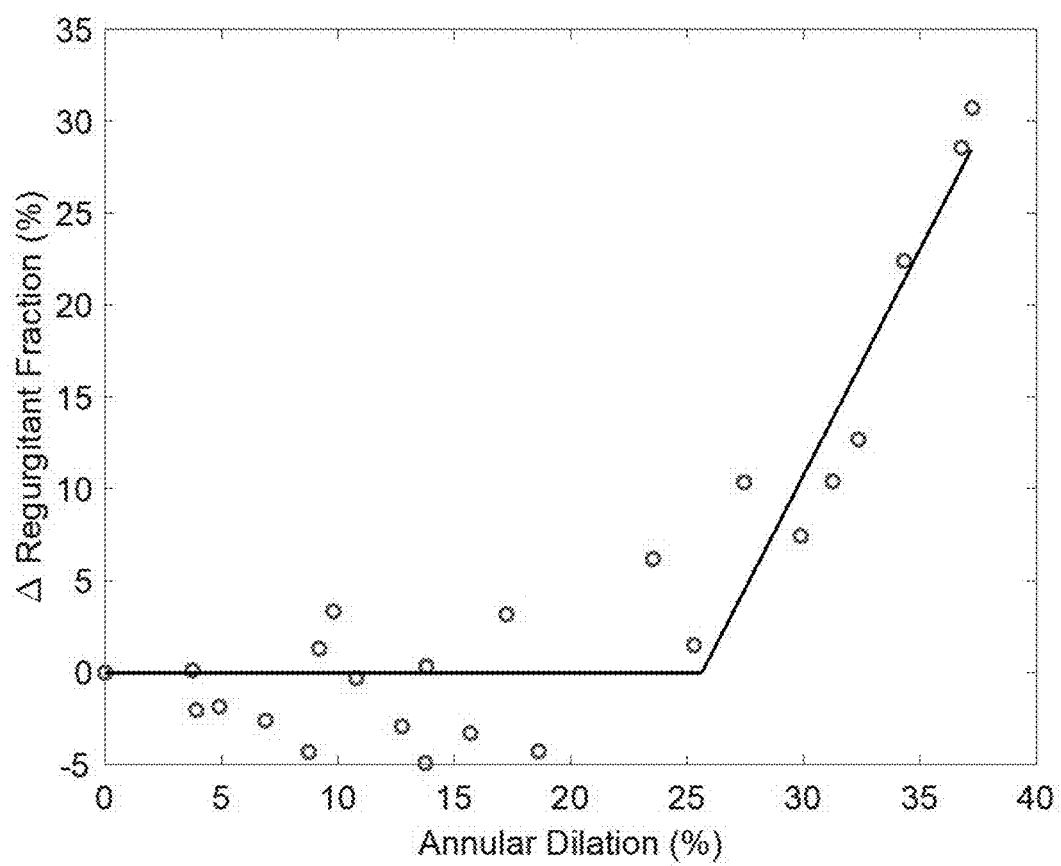
FIG. 3A is a graph showing piece-wise least-squares linear regression fit of regurgitant fraction (with respect to baseline regurgitation) versus percent annular dilation: $G=0$ when $d<25.6$; $G=2.5*d-64$ when $d \geq 25.6$ ($R2=0.90$), where d is the percent dilation and G is the regurgitant fraction increase from baseline.
Figure 3B:
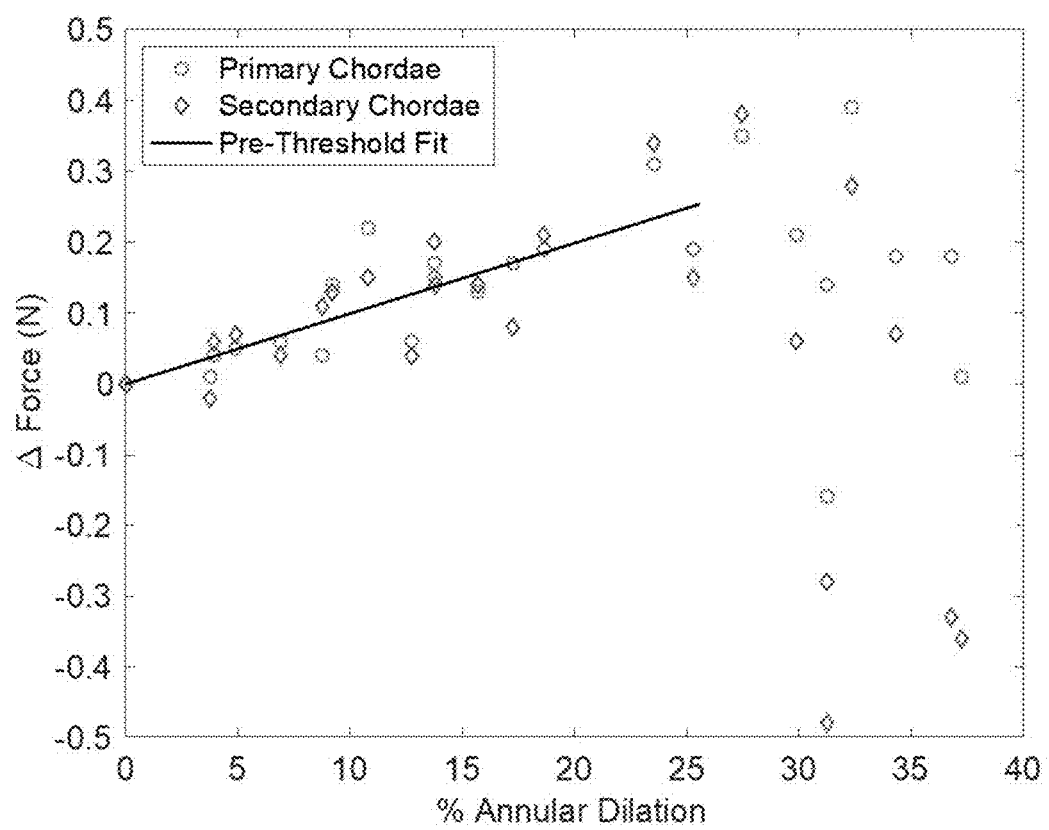
FIG. 3B is a graph showing composites of primary and secondary chordal forces (with respect to baseline forces) versus percent annular dilation. Least-squares linear regression fit with annular dilation lower than the 25.6% dilation threshold: equation.

A plot of the change in forces on the chordae, measured with respect to baseline levels, versus percent annular dilation is shown in FIG. 3B. For each valve 50, the primary chordae forces were averaged, and the secondary chordae were averaged. A least-squares linear regression model was applied to the data with annular dilation less than the 25.6% dilation threshold identified in the regurgitant fraction versus dilation analysis, resulting in the following equation: ΔF=0.011*d ($R^2$=0.75, p=0.002), where ΔF is the change in chordal force from baseline and d is the percent annular dilation. A least-squares linear regression model applied to the post-threshold data gives the following equation, ΔF=−0.028*d+0.94 ($R^2$=0.16, p=0.073). Though the data shows a general downward trend post-threshold, this slope is not significant due to the high variation in forces with increased MR.

Figure 4A:
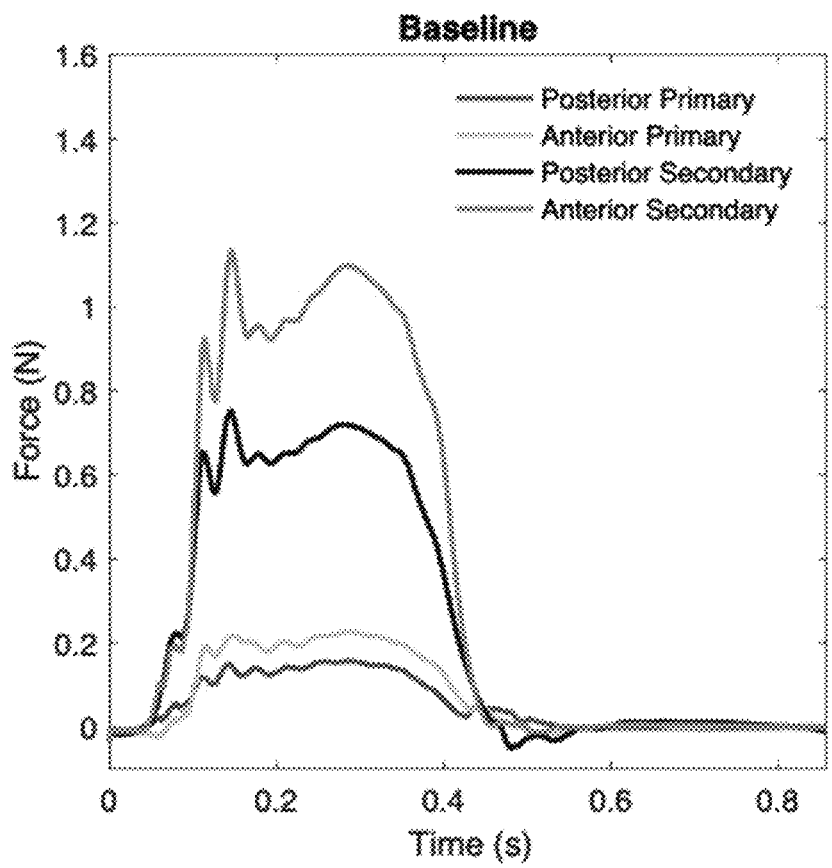
FIGS. 4A-4C are graphs showing representative force tracings for composites of each class of chordae for a single valve at baseline (FIG. 4A), at the maximum dilation point prior to the dilation threshold (FIG. 4B), and at maximum dilation (FIG. 4C).
Figure 4B:
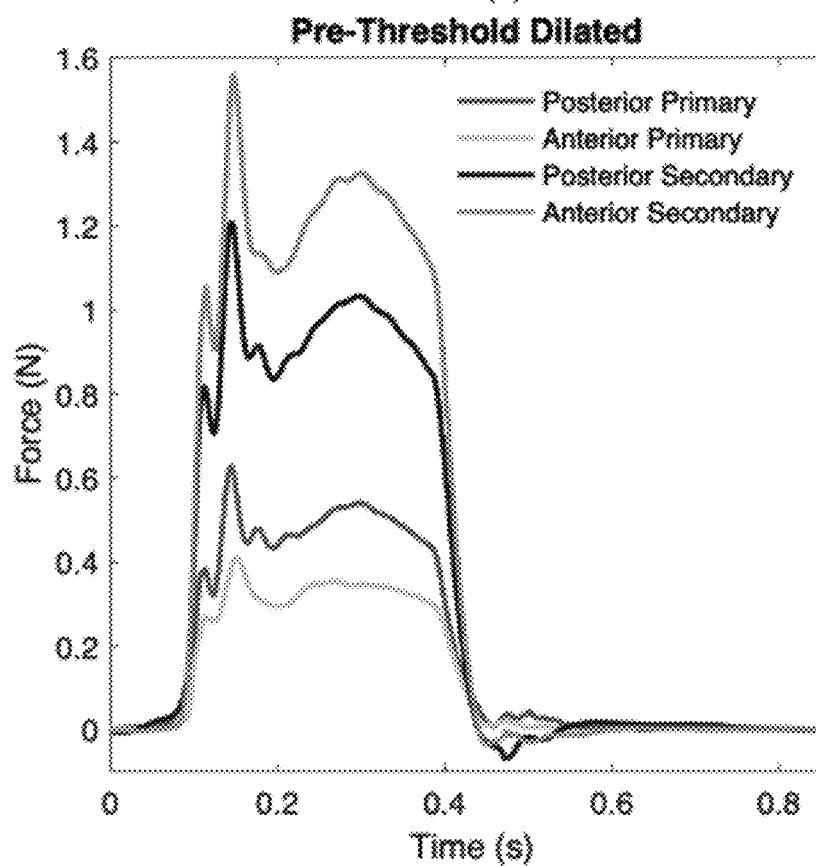
Figure 4C:
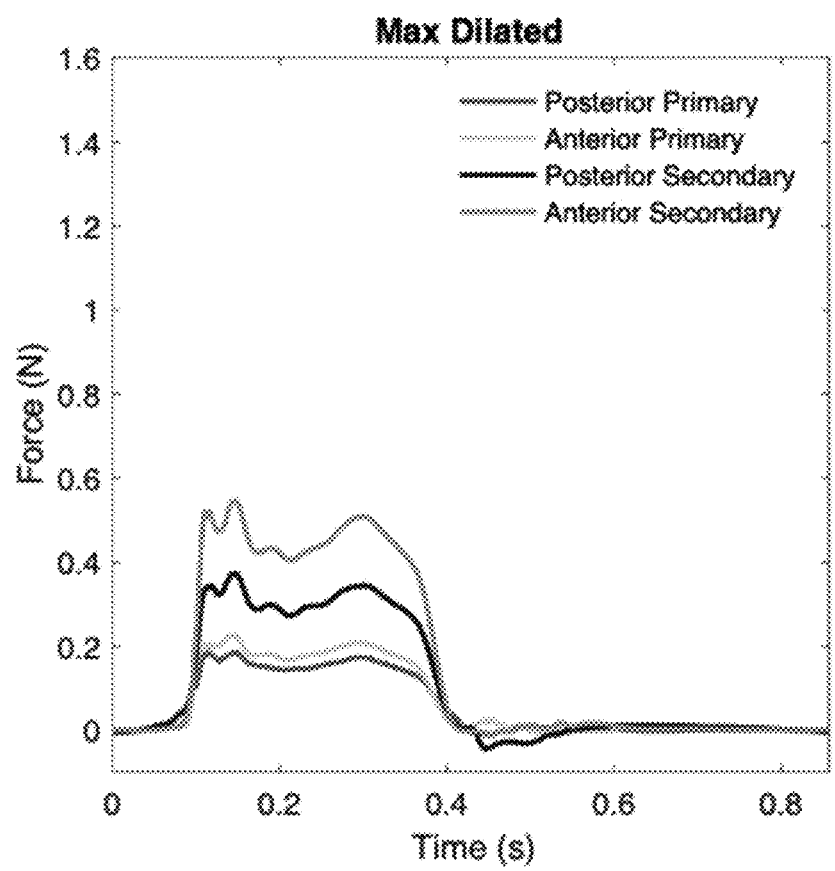

Three representative force tracings for one of the mitral valves 50 tested are shown in FIGS. 4A-4C—baseline forces (FIG. 4A), forces at the maximum dilation point before the annular dilation threshold (FIG. 4B), and forces at the maximum dilation post-threshold (FIG. 4C). The force tracings correspond to the forces over the course of one cardiac cycle.

There was no significant difference between the measured pressures and flows when annular dilation remained below the identified threshold value. However, as the annulus was dilated above the threshold, the hemodynamics change as MR increases. FIG. 7 includes a Table 1 that contains the hemodynamic data for the following states: baseline, pre-threshold dilation, and maximum dilation post-threshold. A repeated-measures Friedman test reported no significant regurgitant fraction difference between baseline and pre-threshold states (p=0.519) but a significantly higher regurgitant fraction in the maximum dilation state compared to baseline (p=0.024).

Figure 5A:
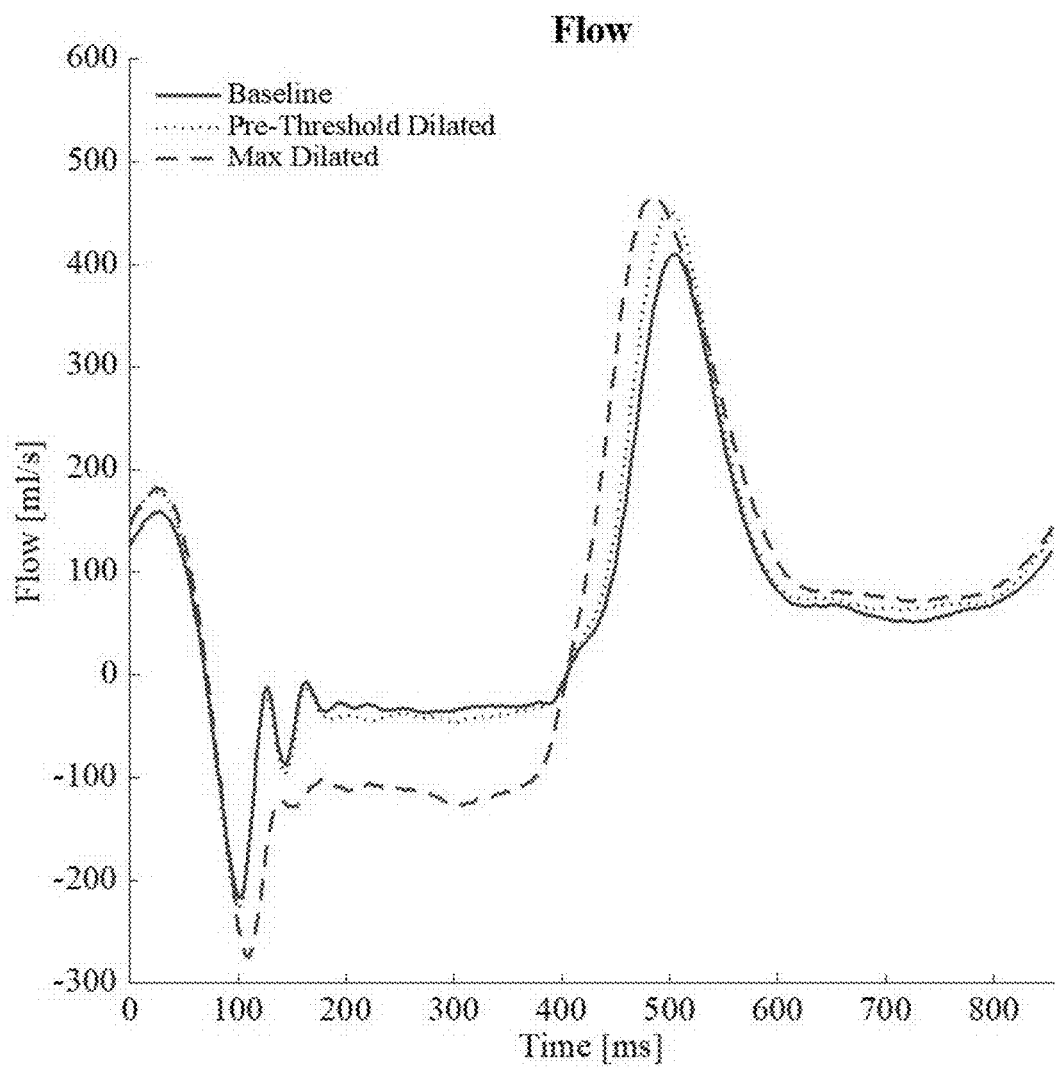
FIG. 5A is a graph showing that mean flow tracings showed no significant difference between the regurgitant fraction at baseline and prior to the 25% annular dilation threshold, but the regurgitant fraction was significantly higher at maximum dilation compared to baseline.
Figure 5B:
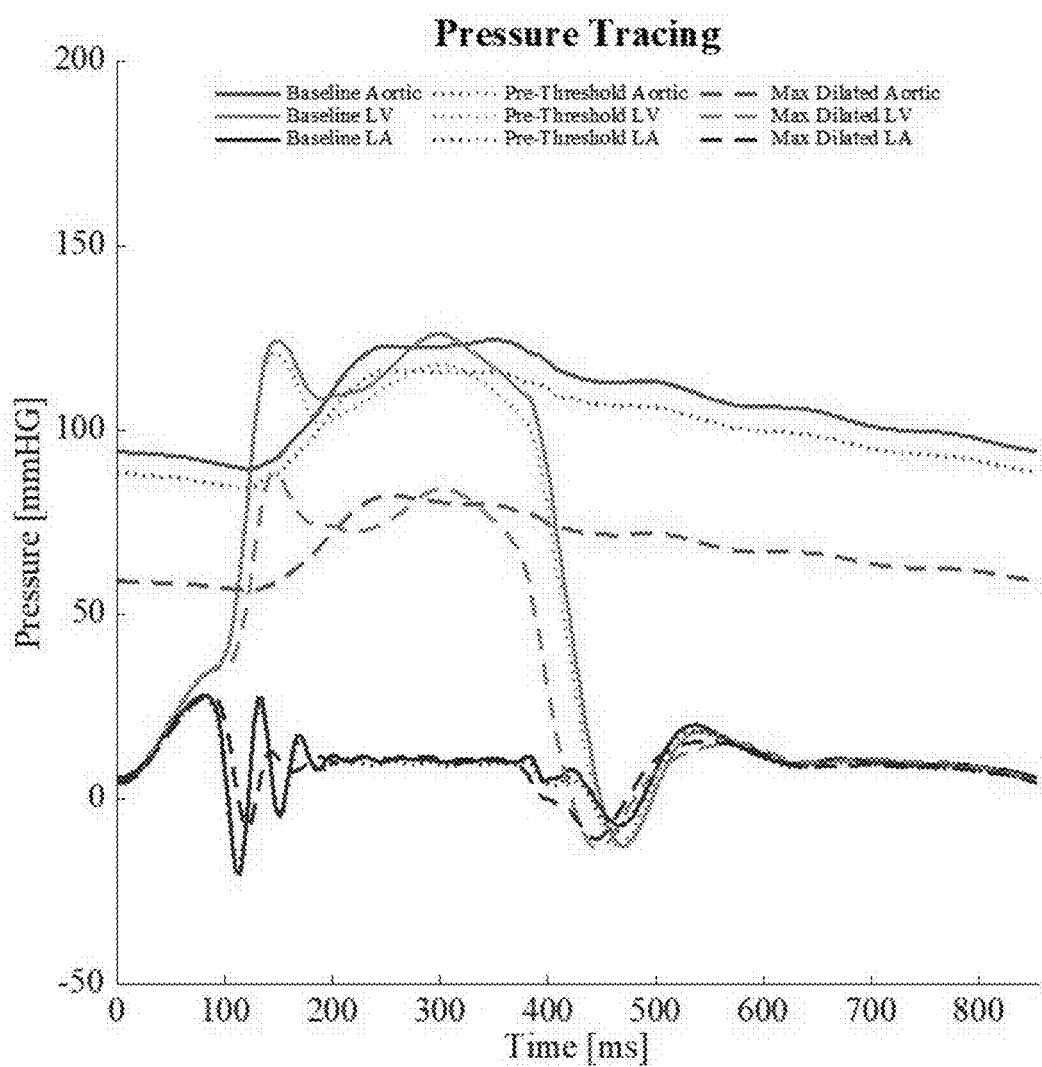
FIG. 5B is a graph showing that mean pressure tracings also confirmed that the aortic, left ventricular (LV), and left atrial (LA) pressures remained at baseline levels prior to the threshold, but mean aortic and LV pressures were lower at maximum dilation. The shaded area represents standard deviation.
Figure 6A:
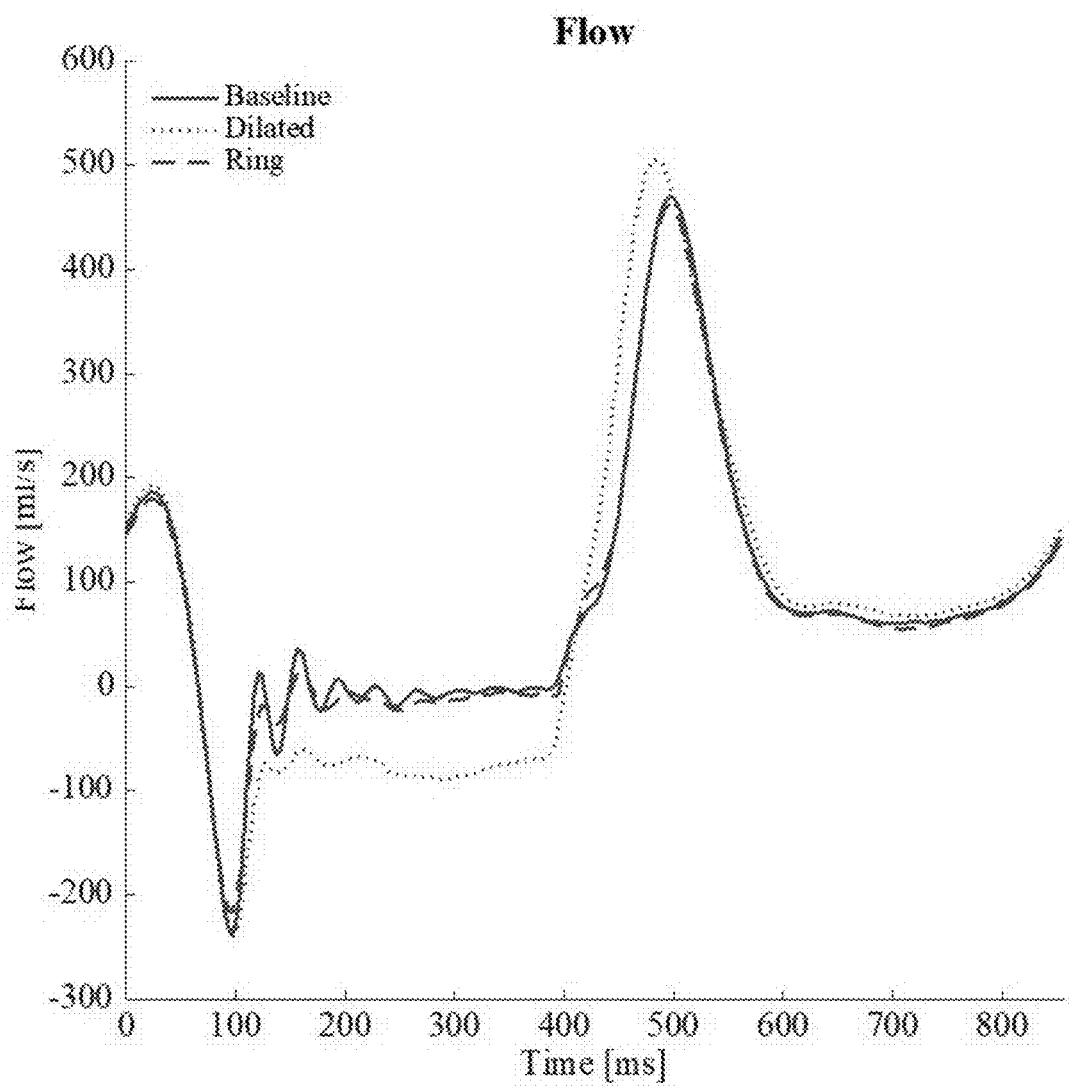
FIG. 6A is graph showing mean flow tracings at baseline, after maximum dilation, and after repair with an annuloplasty ring. Flow was restored to baseline levels after repair.
Figure 6B:
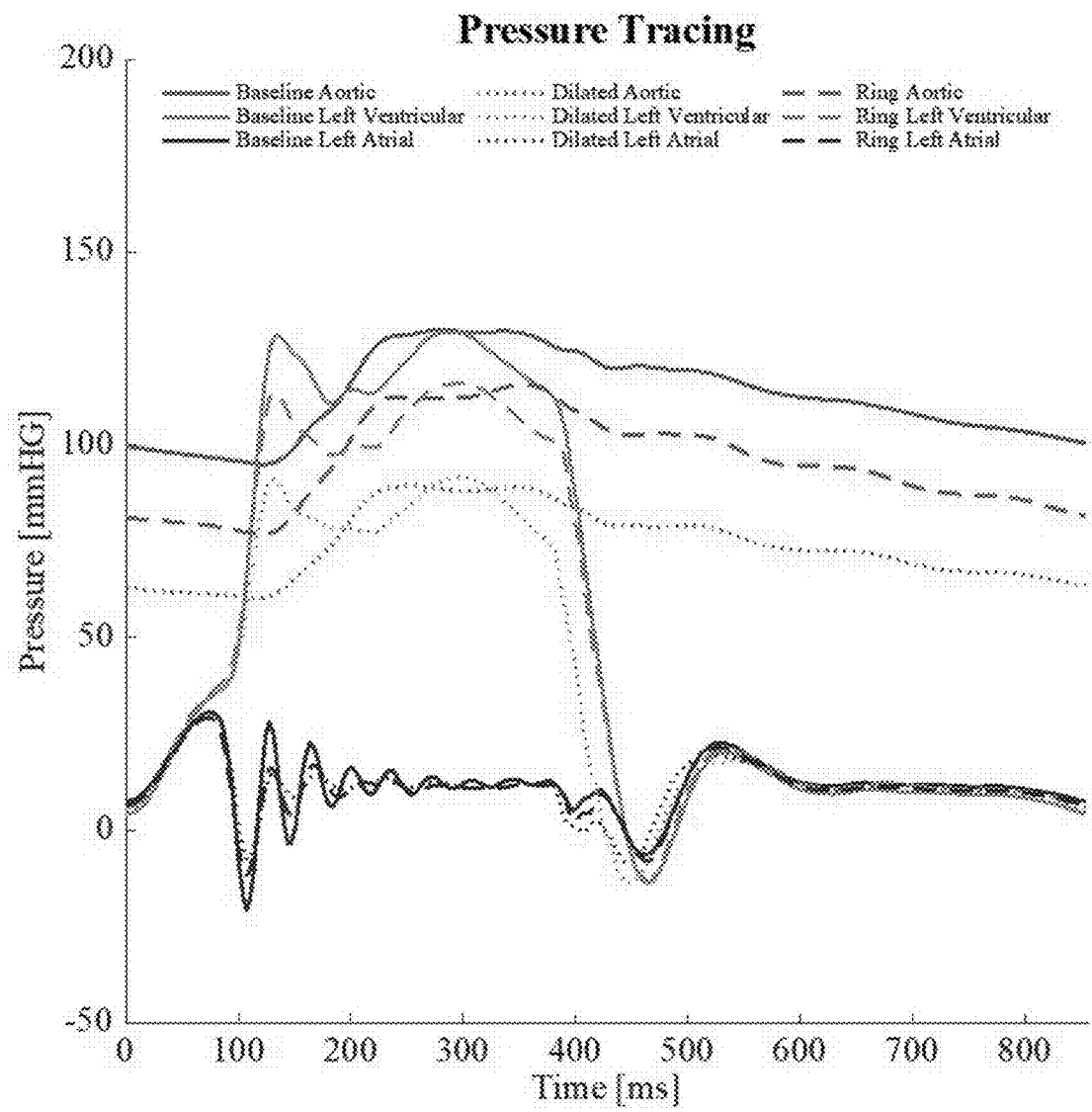
FIG. 6B is a graph showing mean pressure tracings illustrating that the aortic, left ventricular, and left atrial pressures were partially restored to baseline levels after repair.

The hemodynamic results are also illustrated in FIGS. 5A and 5B, which show the flow and pressure data for the same three states with the shaded region corresponding to standard deviation. Both flow and pressure remain relatively unchanged between baseline and pre-threshold states, but were altered between the pre-threshold and maximum dilation states. Additionally, the supplemental annuloplasty ring experiment results are shown in FIGS. 6A and 6B. The measured pressures and flows corresponded to expected in vivo values, with both flow and pressure appearing to be largely restored after the annuloplasty. The regurgitant fraction was measured to be 12% at baseline, 34% when dilated, and 14% post-repair.

Discussion

Much of the previous literature devoted to studying MR focused on the relationship between regurgitant fraction and annular size (rather than percent annular dilation), and thus no threshold for the onset of MR could be easily identified. However, there have been select studies with data on the regurgitant volume versus the percent annular dilation, which do show a threshold for the onset of significant MR. This threshold is likely due to a relatively large coaptation surface in healthy mitral valves, which allows for a moderate degree of annulus dilation before leaflet coaptation is severely impaired. Note that diseased valves, especially those with excess myxomatous leaflet tissue, may have a different threshold value. Future studies could examine the effect of annular dilation on a variety of diseased valves.

The MR onset threshold was clearly present in this study in the regurgitant fraction (with respect to baseline) versus percent annular dilation data. The piecewise function used to determine the 25.6% threshold value as well as the slope for the post-threshold data produced a better fit with a higher $R^2$ and lower p-value than both a linear regression model and a quadratic regression model. With an increased sample size and the inclusion of human valves, identifying the percent annular dilation threshold could be used as a predictor for patients who are at risk for severe MR. Annular size has been proposed as a metric to predict progression from moderate to severe MR, but this threshold value of percent annular dilation that results in severe MR could provide a more accurate predictor.

There was also an effect of MR onset on the chordal forces. As dilation increases prior to the threshold, the forces on both primary and secondary chordae tendineae increased. This increase in force was as expected. In cases of chronic functional MR, these chordal forces would likely continue to increase after MR onset as the heart remodels to maintain pressure despite the increasing regurgitant fraction. However, the chordal forces did not continue to increase in this study because the ex vivo dilation device modeled acute MR, where the increasing regurgitant fraction results in a sharp decrease in LV and aortic pressures. Importantly, the wide range of forces present post-threshold illustrates the turbulent effect of MR on the mitral valve apparatus, increasing forces on some chordae while decreasing the forces on others. These chordal forces can be minimized with an optimal annuloplasty ring. Thus, using hemodynamics and chordal force measurements as metrics, a multitude of annuloplasty devices can be tested and analyzed with this dilation device and experimental protocol.

In additional embodiments, the dilation devices 10 and 80 may be utilized with a tricuspid valve, in substantially the same manner as described herein for a mitral valve.

In other embodiments, instead of attaching (such as be suturing) the valve annulus 52 to the dilation device 10, 80, a cuff of the left atrium just beyond the valve annulus 52 is attached to the dilation device 10, 80, in substantially the same manner as attaching the valve annulus 52 to the dilation device 10, 80. While the atrium may be more prone to tearing, the atrium provides some elasticity (similar to the effect of the biasing mechanisms, described herein) such that repairs can be made (i.e. annuloplasty ring) and the atrium cuff can stretch to accommodate this even if the dilation device 10, 80 is locked in place.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

What is claimed is:

1. A dilation device for modeling mitral regurgitation in a mitral valve, comprising:
   an annular housing surrounding an aperture;
   an anterior blade mounted to the housing and defining an inner edge adjacent the aperture;
   a plurality of posterior blades mounted to the housing and defining an inner edge adjacent the aperture, the posterior blades movable to dilate a valve mounted to the blades.

2. The dilation device of claim 1, wherein the inner edge of the anterior blade is substantially straight, and the inner edge of the plurality of posterior blades defines a substantially circular curve.

3. The dilation device of claim 1, further comprising a plurality of perforations along the respective inner edges of the anterior blade and the plurality of posterior blades for receiving sutures to secure a valve to the anterior blade and the posterior blades.

4. The dilation device of claim 1, wherein the housing comprises a pivot plate movable relative to a base plate, and wherein each of the posterior blades comprises a first end coupled to the pivot plate such that movement of the pivot plate causes the posterior blades to move between a relaxed position and a dilating position.

5. The dilation device of claim 4, wherein the base plate comprises a plurality of slots, and each of the posterior blades comprises a second end coupled to a respective slot in the base plate such that the second end moves radially inward and outward when the pivot plate moves.

6. The dilation device of claim 5, wherein the pivot plate is rotatable relative to the base plate to cause the posterior blades to move radially outward to dilate an anterior annulus of a mitral valve mounted to the posterior blades.

7. The dilation device of claim 4, further comprising a biasing mechanism coupled to the posterior blades which biases the posterior blades toward the dilating position.

8. The dilation device of claim 7, wherein the biasing mechanism is a spring coupled to the pivot plate.

9. The dilation device of claim 1, wherein the anterior blade and posterior blades are laterally flexible to allow the anterior blade and posterior blades to flex laterally to allow substantially natural motion of a mitral valve during a cardiac cycle of a mitral valve.

10. A system for modeling mitral regurgitation in a mitral valve, comprising:
    a dilation device comprising an annular housing surrounding an aperture; a first anterior blade mounted to the housing and defining a substantially straight inner edge adjacent the aperture; and a plurality of posterior blades mounted to the housing and defining a curved inner edge adjacent the aperture, the posterior blades movable to dilate a valve mounted to the blades; and
    a heart simulator comprising a housing for mounting the dilation device at a location corresponding to a mitral valve of a heart; and a pump for directing fluid through the housing such that the fluid passes through a valve mounted to the dilation device.

11. A method for modeling mitral regurgitation in a mitral valve, comprising:
    providing a dilation device comprising an annular housing surrounding an aperture; a first anterior blade mounted to the housing and defining a substantially straight inner edge adjacent the aperture; and a plurality of posterior blades mounted to the housing and defining a curved inner edge adjacent the aperture, the posterior blades movable to dilate a valve mounted to the blades;
    securing an annulus of a valve to the blades of the dilation device such that valve is disposed within the aperture; and
    actuating the dilation device to cause the posterior blades to dilate a posterior region of the annulus.

12. The method of claim 11, wherein securing the annulus comprises directing one or more sutures through perforations along the inner edge and the annulus.

13. The method of claim 11, wherein, during actuation of the dilation device, an anterior region of the annulus does not dilate substantially.

14. The method of claim 11, further comprising:
    mounting the dilation device with the valve secured thereto within a heart simulator; and
    directing fluid through the simulator such that the fluid passes through a valve mounted to the dilation device to simulate operation of the valve.

15. The method of claim 14, wherein the dilation device is actuated to sequentially increase the amount of posterior dilation of the valve to analyze mitral regurgitation.

16. A dilation device for modeling mitral regurgitation in a mitral valve, comprising:
    a base plate having a plate aperture and a recess surrounding the aperture;
    a mounting ring having a ring aperture, the mounting ring mounted in the recess of the base plate with the ring aperture aligned with the plate aperture;
    a plurality of adjustment pins mounted on the base plate spaced angularly around the mounting ring, each of the adjustment pins configured to receive a respective adjustment cord attachable to a valve mounted on the mounting ring and adjustable to selectably dilate the valve.

17. The dilation device of claim 16, wherein the adjustment pins each comprise a tuning key, each tuning key having a rotatable knob coupled to a rotatable post via a gear set such that rotation of the knob rotates the post, the post for receiving a respective adjustment cord.

18. The dilation device of claim 17, wherein the gear set comprises a worm gear and a mating pinion gear.

19. The dilation device of claim 16, wherein the mounting ring is formed of a pliable, elastomeric material for receiving sutures to secure a valve to the mounting ring.

20. The dilation device of claim 16, further comprising a plurality of biasing mechanisms, each of the biasing mechanisms coupled to a respective adjustment cord.

* * * * *